US006867006B2

(12) United States Patent
Li et al.

(10) Patent No.: US 6,867,006 B2
(45) Date of Patent: Mar. 15, 2005

(54) ANTIBODIES TO HUMAN CHEMOTACTIC PROTEIN

(75) Inventors: Haodong Li, Gaithersburg, MD (US); Steven M. Ruben, Olney, MD (US); Granger Sutton, III, Columbia, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 230 days.

(21) Appl. No.: 10/141,965

(22) Filed: May 10, 2002

(65) Prior Publication Data

US 2002/0182200 A1 Dec. 5, 2002

Related U.S. Application Data

(60) Division of application No. 09/453,416, filed on Dec. 3, 1999, now Pat. No. 6,419,917, which is a division of application No. 09/044,855, filed on Mar. 20, 1998, now Pat. No. 6,100,389, which is a continuation-in-part of application No. 08/479,126, filed on Jun. 7, 1995, now Pat. No. 5,866,373, which is a continuation-in-part of application No. 08/424,425, filed on Apr. 21, 1995, now abandoned, and a continuation-in-part of application No. PCT/US94/05384, filed on May 16, 1994.

(51) Int. Cl.[7] .................. C07K 16/00; C07K 16/18; C07K 16/22; C07K 16/24; C07K 16/26
(52) U.S. Cl. ............... 435/7.1; 530/387.1; 530/387.3; 530/388.1; 530/388.15; 530/388.23; 530/388.24; 530/389.1; 530/389.2; 530/391.1; 530/391.3
(58) Field of Search .................. 435/7.1; 560/387.1, 560/387.3, 387.9, 388.1, 388.15, 388.23, 388.24, 389.1, 389.2, 391.1, 391.3

(56) References Cited

U.S. PATENT DOCUMENTS

| 5,179,078 A | 1/1993 | Rollins et al. |
| 5,237,051 A | 8/1993 | Garbers et al. |
| 5,350,836 A | 9/1994 | Kopchick et al. |
| 5,382,658 A | 1/1995 | Kronis et al. |
| 5,459,128 A | 10/1995 | Rollins et al. |
| 5,866,373 A | 2/1999 | Li et al. |
| 5,880,263 A | 3/1999 | Li et al. |
| 6,028,169 A | 2/2000 | Kreider et al. |
| 6,075,124 A | 6/2000 | Li et al. |
| 6,100,389 A | 8/2000 | Li et al. |
| 6,174,995 B1 | 1/2001 | Li et al. |
| 6,379,926 B1 | 4/2002 | Kreider et al. |
| 6,419,917 B1 | 7/2002 | Li et al. |

FOREIGN PATENT DOCUMENTS

| CA | 2 152 141 | 12/1996 |
| EP | 0 488 900 | 6/1992 |
| WO | WO-98/08777 | 8/1990 |
| WO | WO 92/20372 | 11/1992 |
| WO | WO 95/07985 | 3/1995 |
| WO | WO 95/31467 | 11/1995 |
| WO | WO 96/38559 | 12/1996 |
| WO | WO 96/40762 | 12/1996 |
| WO | WO 97/15594 | 5/1997 |
| WO | WO-98/44118 | 10/1998 |

OTHER PUBLICATIONS

Beall, C.J., et al., "Conversion of Monocyte Chemoattractant Protein–1 into a Neutrophil Attractant by Substitution of Two Amino Acids," *J. Biol. Chem.* 267:3455–3459, American Society for Biochemistry and Molecular Biology, Inc. (1992).

Berkhout, T.A., et al., "Cloning, in Vitro Expression, and Functional Characterization of a Novel Human CC Chemokine of the Monocyte Chemotactic Protein (MCP) Family (MCP–4) That Binds and Signals through the CC Chemokine Receptor 2B," *J. Biol. Chem.* 272:16404–16413, American Society for Biochemistry and Molecular Biology, Inc. (Jun. 1997).

Bischoff, S.C., et al., "Monocyte Chemotactic Protein 1 Is a Potent Activator of Human Basophils," *J. Exp. Med.* 175:1271–1275, Rockefeller University Press (1992).

Bork, P., and Bairoch, A., "Go hunting in sequence databases but watch out for the traps," *Trends Genet.* 12:425–427, Elsevier Science B.V. (Oct. 1996).

Bork, P., "Powers and Pitfalls in Sequence Analysis: The 70% Hurdle," *Genome Res.* 10:398–400, Cold Spring Harbor Laboratory Press (Apr. 2000).

Bottazzi, B., et al., "A chemoattractant expressed in human sarcoma cells (tumor–derived chemotactic factor, TDCF) is identical to monocyte chemoattractant protein–1/monocyte chemotactic and activating factor (MCP–1/MCAF)," *Int. J. Cancer* 45:795–797, Wiley–Liss, Inc. (1990).

Bowie, J.U., et al., "Deciphering the Message in Protein Sequences: Tolerance to Amino Acid Substitutions," *Science* 247:1306–1310, American Association for the Advancement of Science (1990).

Brenner, S.E., "Errors in genome annotation," *Trends Genet.* 15:132–133, Elsevier Science B.V. (Apr. 1999).

Brieland, J.K., et al., "Effect of Acute Inflammatory Lung Injury on the Expression of Monocyte Chemoattractant Protein–1 (MCP–1) in Rat Pulmonary Alveolar Macrophages," *Am. J. Respir. Cell Mol. Biol.* 7:134–139, American Lung Association (1992).

(List continued on next page.)

*Primary Examiner*—Elizabeth Kemmerer
(74) *Attorney, Agent, or Firm*—Human Genome Sciences, Inc.

(57) ABSTRACT

A human chemotactic polypeptide, DNA(RNA) encoding it, and a procedure for producing such a polypeptide by recombinant techniques are disclosed. Also disclosed are methods of using the polypeptide for a number of purposes, including: stem cell mobilization, myeloprotection, neuronal protection, treating tumors, wound healing, treating parasitic infection, and regulating hematopoiesis. Also disclosed are polypeptide antagonists and diagnostic assays for identifying mutations in nucleic acid sequence encoding a polypeptide of the present invention and for detecting altered levels of the polypeptide of the present invention for detecting diseases are also disclosed.

80 Claims, 10 Drawing Sheets

OTHER PUBLICATIONS

Brieland, J.K., et al., "Expression of Monocyte Chemoattractant Protein–1 (MCP–1) by Rat Alveolar Macrophages during Chronic Lung Injury," *Am. J. Respir. Cell Mol. Biol.* 9:300–305, American Lung Association (1993).

Brown, Z., et al., "IL–1 receptor antagonist inhibits monocyte chemotactic peptide–1 generation by human mesangial cells," *Kidney Int.* 42:95–101, Blackwell Scientific Publications (1992).

Colditz, I., et al., "*In Vivo* Inflammatory Activity of Neutrophil–Activating Factor, a Novel Chemotactic Peptide Derived from Human Monocytes," *Am. J. Pathol.* 134:755–760, American Association of Pathologists (1989).

Daniel, C., et al., "Mapping of Linear Antigenic Sites on the S Glycoprotein of a Neurotropic Murine Coronavirus with Synthetic Peptides: A Combination of Nine Prediction Algorithms Fails To Identify Relevant Epitopes and Peptide Immunogenicity Is Drastically Influenced by the Nature of the Protein Carrier," *Virology* 202:540–549, Academic Press, Inc. (Aug. 1994).

Decock, B., et al., "Identification of the Monocyte Chemotactic Protein from Human Osteosarcoma Cells and Monocytes Detection of a Novel N–Terminally Processed Form," *Biochem. Biophys. Res. Commun.* 167:904–909, Academic Press, Inc. (1990).

Doerks, T., et al., "Protein annotation: detective work for function prediction," *Trends Genet.* 14:248–250, Elsevier Science B. V. (Jun. 1998).

Forssmann, U., et al., "Eotaxin–2, a Novel CC Chemokine that Is Selective for the Chemokine Receptor CCR3, and Acts Like Eotaxin on Human Eosinophil and Basophil Leukocytes," *J. Exp. Med.* 185:2171–2176, Rockefeller University Press (Jun. 1997).

Furutani, Y., et al., "Cloning and Sequencing of the cDNA for Human Monocyte Chemotactic and Activating Factor (MCAF)," *Biochem. Biophys. Res. Commun.* 159:249–255, Academic Press, Inc. (1989).

Garcia–Zepeda, E.A., et al., "Human Monocyte Chemoattractant Protein (MCP)–4 Is a Novel CC Chemokine with Activities on Monocytes, Eosinophils, and Basophils Induced in Allergic and Nonallergic Inflammation That Signals Throught the CC Chemokine Receptors (CCR)–2 and –3," *J. Immunol.* 157:5613–5626, American Association of Immunologists, Inc. (Dec. 1996).

George, D.G., et al., "Current Methods in Sequence Comparison and Analysis," in *Macromolecular Sequencing and Synthesis, Selected Methods and Applications*, Schlesinger, D.H., ed., Alan R. Liss, Inc., New York, New York, pp. 127–149 (1988).

Gong, J.–M., and Clark–Lewis, I., "Antagonists of Monocyte Chemoattractant Protein 1 Indentified by Modification of Functionally Critical $NH_2$–terminal Residues," *J. Exp. Med.* 181:631–640, Rockefeller University Press (Feb. 1995).

Gong, J.–H., et al., "RANTES and MCP–3 Antagonists Bind Multiple Chemokine Receptors," *J. Biol. Chem.* 271:10521–10527, American Society for Biochemistry and Molecular Biology, Inc. (May 1996).

Gronenborn, A.M., and Clore, G.M., "Modeling the three–dimensional structure of the monocyte chemo–attractant and activating protein MCAF/MCP–1 on the basis of the solution structure of interleukin–8," *Protein Eng.* 4:263–269, Oxford University Press (1991).

Jose, P.J., et al., "Eotaxin: A Potent Eosinophil Chemoattractant Cytokine Detected in a Guinea Pig Model of Allergic Airways Inflammation," *J. Exp. Med.* 179:881–887, Rockefeller University Press (Mar. 1994).

Kao, J., et al., "Endothelial Monocyte–activating Polypeptide II. A Novel Tumor–Derived Polypeptide That Activates Host–Response Mechanisms," *J. Biol. Chem.* 267:20239–20247, American Society for Biochemistry and Molecular Biology, Inc. (1992).

Kawahara, R.S., and Deuel, T.F., "Platelet–derived Growth Factor–inducible Gene JE Is a Member of a Family of Small Inducible Genes Related to Platelet Factor 4," *J. Biol Chem.* 264:679–682, American Society for Biochemistry and Molecular Biology, Inc. (1989).

Koch, A.E., et al., "Enhanced Production of Monocyte Chemoattractant Protein–1 in Rheumatoid Arthritis," *J. Clin. Invest.* 90: 772–779, American Society for Clinical Investigation, Inc. (1992).

Kuna, P., et al., "Monocyte Chemotactic and Activating Factor Is a Potent Histamine–releasing Factor for Human Basophils," *J. Exp. Med.* 175:489–493, Rockefeller University Press (1992).

Marston, F.A.O., "The purification of eukaryotic polypeptides synthesized in *Escherichia coli*," *Biochem J.* 240:1–12, London Portland Press on Behalf of The Biochemical Society (1986).

Matsushima, K., et al., "Molecular Cloning of a Human Monocyte–Derived Neutrophil Chemotactic Factor (MDNCF) and the Induction of MDNCF mRNA by Interleukin 1 and Tumor Necrosis Factor," *J. Exp. Med.* 167:1883–1893, Rockefeller University Press (1988).

Matsushima, K., et al., "Purification and Characterization of a Novel Monocyte Chemotactic and Activating Factor Produced by a Human Myelomonocytic Cell Line," *J. Exp. Med.* 169:1485–1490, Rockefeller University Press (1989).

Mehrabian, M., et al., "Localization of Monocyte Chemotactic Protein–1 Gene (SCYA2) to Human Chromosome 17q11.2–q21.1," *Genomics* 9:200–203, Academic Press, Inc. (1991).

Minty, A., et al., "Molecular cloning of the MCP–3 chemokine gene and regulation of its expression," *Eur. Cytokine Netw.* 4:99–110, John Libbey Eurotext Ltd. (1993).

Morgan, J.G., et al., "Cloning of the cDNA For The Serine Protease Homolog CAP37/Azurocidin, A Microbicidal and Chemotactic Protein from Human Granulocytes," *J. Immunol.* 147:3210–3214, American Association of Immunologists, Inc. (1991).

Nelken, N.A., et al., "Monocyte Chemoattractant Protein–1 in Human Atheromatous Plaques," *J. Clin. Invest.* 88:1121–1127, American Society for Clinical Investigation, Inc. (1991).

Ngo, J.T., et al., "Computational Complexity, Protein Structure Prediction, and the Levinthal Paradox,"In: *The Protein Folding Problem and Tertiary Structure Prediction*, Merz, Jr., K. and Le Grand, S., eds., Birkhäuser, Boston, Massachusetts, pp. 491–495 (1994).

Opdenakker, G., et al., "Human monocyte chemotactic protein–3 (MCP–3) : molecular cloning of the cDNA and comparison with other chemokines," *Biochem. Biophys. Res. Comm. 191*:535–542, Academic Press, Inc. (1993).

Pereira, H.A., et al., "CAP37, a Human Neutrophil–derived Chemotactic Factor with Monocyte Specific Activity," *J. Clin. Invest. 85*:1468–1476, American Society for Clinical Investigation, Inc. (1990).

Ransohoff, R.M., et al., "Astrocyte expression of mRNA encoding cytokines IP–10 and JE/MCP–1 in experimental autoimmune encephalomyelitis," *FASEB J. 7*:592–600, Federation of American Societies for Experimental Biology (1993).

Robinson, E.A., et al., "Complete amino acid sequence of a human monocyte chemoattractant, a putative mediator of cellular immune reactions," *Proc. Natl. Acad. Sci. USA 86*:1850–1854, National Academy of Sciences (1989).

Rolfe, M.W., et al., "Expression and regulation of human pulmonary fibroblast–derived monocyte chemotactic peptide–1," *Am. J. Physiology 263*:L536–L545, American Physiological Society (1992).

Rollins, B.J., et al., "Cloning and expression of JE , a gene inducible by platelet–derived growth factor and whose product has cytokine–like properties," *Proc. Natl. Acad. Sci. USA 85*:3738–3742, National Academy of Sciences (1988).

Rollins, B.J., et al., "The Human Homolog of the JE Gene Encodes a Monocyte Secretory Protein," *Mol. Cell. Biol. 9*:4687–4695, American Society for Microbiology (1989).

Rudinger, J., "Characteristics of the amino acids as components of a peptide hormone sequence," In: *Peptide Hormones*, Parsons, J.A., ed., University Park Press, Baltimore, Maryland, pp. 1–7 (1976).

Russell, M.E., et al., "Early and persistent induction of monocyte chemoattractant protein 1 in rat cardiac allografts," *Proc. Natl. Acad. Sci. USA 90*:6086–6090, National Academy of Sciences (1993).

Sacerdote, P., et al., "Cholecystokinin and the Immune System: Receptor–Mediated Chemotaxis of Human and Rat Monocytes," *Peptides 9*:29–34, Pergamon Press (1988).

Schall, T.J., "Biology Of The RANTES/SIS Cytokine Family," *Cytokine 3*:165–183, W.B. Saunders Co. (1991).

Schulz, G.E., and Schirmer, R.H., "Empirical Similarities Between Amino Acid Residues," in *Principles of Protein Structure*, Springer–Verlag, New York, New York, pp. 14–16 (1979).

Shyy, Y.–J., et al., "Structure of Human Monocyte Chemotactic Protein Gene and Its Regulation by TPA," *Biochem. Biophys. Res. Commun. 169*:346–351, Academic Press, Inc. (1990).

Skolnick, J., and Fetrow, J.S., "From genes to protein structure and function: novel applications of computational approaches in the genomic era," *Trends Biotechnol. 18*:34–39, Elsevier Science B.V. (Jan. 2000).

Smith, T.F., and Zhang, X., "The challenge of genome sequence annotation or 'The devil is in the details,'" *Nat. Biotechnol. 15*:1222–1223, Nature Publishing Co. (Nov. 1997).

Strieter, R.M., et al., "Disparate Gene Expression of Chemotactic Cytokines by Human Mononuclear Phagocytes," *Biochem. Biophys. Res. Commun. 166*:886–891, Academic Press, Inc. (1990).

Uguccioni, M., et al., "Monocyte Chemotactic Protein 4 (MCP–4), a Novel Structural and Functional Analogue of MCP–3 and Eotaxin," *J. Exp. Med. 183*:2379–2384, Rockefeller University Press (May 1996).

Van Damme, J., et al., "Production and identification of natural monocyte chemotactic protein from virally infected murine fibroblasts: Relationship with the product of the mouse competence (JE) gene," *Eur. J. Biochem. 199*:223–229, Blackwell Science Ltd. (1991).

Van Damme, J., et al., "Structural and Functional Identification of Two Human, Tumor–derived Monocyte Chemotactic Proteins (MCP–2 and MCP–3) Belonging to the Chemokine Family," *J. Exp. Med. 176*:59–65, Rockefeller University Press (1992).

Villiger, P.M., et al., "Monocyte chemoattractant Protein–1 (MCP–1) Expression in Human Articular Cartilage," *J. Clin. Invest. 90*:488–496, American Society for Clinical Investigations, Inc. (1992).

Wells, J.A., "Additivity of Mutational Effects in Proteins," *Biochem. 29*:8509–8517, American Chemical Society (1990).

Wempe, F., et al., "Gene Expression and cDNA Cloning Identified a Major Basic Protein Constituent of Bovine Seminal Plasma as Bovine Monocyte–Chemoattractant Protein–1 (MCP–1)," *DNA and Cell Biol. 10*:671–679, Mary Ann Liebert, Inc. (1991).

Yan, M., et al., "Two–Amino Acid Molecular Switch in an Epithelial Morphogen That Regulates Binding to Two Distinct Receptors," *Science 290*:523–527, American Association for the Advancement of Science (Oct. 2000).

Yoshimura, T., et al., "Human monocyte chemoattractant protein–1 (MCP–1): Full–length cDNA cloning, expression in mitogen–stimulated blood mononuclear leukocytes, and sequence similarity to mouse competence gene JE," *FEBS Letters 244*:487–493, Elsevier Science B.V. (1989).

Yoshimura, T., et al., "Molecular Cloning of Rat Monocyte Chemoattractant Protein–1 (MCP–1) and Its Expression in Rat Spleen Cells and Tumor Cell Lines," *Biochem. Biophys. Res. Commun. 174*:504–509, Academic Press, Inc. (1991).

Yoshimura, T., and Yuhki, N., "Neutrophil Attractant/Activation Protein–1 And Monocyte Chemoattractant Protein–1 In Rabbit," *J. Immunol. 146*:3483–3488, American Association of Immunologists, Inc. (1991).

WPI Accession No. 92–185765, English Language Abstract of EP 0 488 900 (Document AL1).

Supplementary European Search Report for Application No. EP 94 91 7388, completed Mar. 26, 1997.

International Search Report for Application No. PCT/US98/06401, mailed Jul. 31, 1998.

Wempe, F., et al., "Gene Expression and cDNA Cloning Identified a Major Basic Protein Constituent of Bovine Seminal Plasma as Bovine Monocyte–Chemoattractant Protein–1 (MCP–1)," DNA and Cell Biol 10:671–679, Mary Ann Liebert, Inc. (1991).

Broxmeyer, H.E., et al., "Effects of CC, CXC, C, and CX3C Chemokines on Proliferation of Myeloid Progenitor Cells, and Insights into SDF–1–Induced Chemotaxis of Progenitors," Ann. N.Y. Acad. Sci. 872:142–163, New York Academy of Sciences (Apr. 1999).

Daly, T.J., et al., "High Activity Suppression of Myeloid Progenitor Proliferation by Chimeric Mutants of Interleukin 8 and Platelet Factor 4," J. Biol. Chem. 270:23282–23292, American Society for Biochemistry and Molecular Biology, Inc. (1995).

Gayle, R.B., et al., "Identification of Regions in Interleukin–1 Important for Activity," J. Biol. Chem. 268:22105–22111, American Society for Biochemistry and Molecular Biology, Inc. (1993).

Grzegorzewski, K.J., et al., "Analysis of Eosinophils and Myeloid Progenitor Responses to Modified Forms of MPIF–2," Cytokine 13:209–219, Academic Press, Inc. (Feb. 2001).

Murphy, P.A., "The Molecular Biology of Leukocyte Chemoattractant Receptors," Annul. Rev. Immunol. 12:593–633, Annual Reviews, Inc. (1994).

Patel, V.P., et al., "Molecular and Functional Characterization of Two Novel Human C–C Chemokines as Inhibitors of Two Distinct Classes of Myeloid Progenitors," J. Exp. Med. 185(7):1163–1172, Rockefeller University Press (Apr. 1997).

Salcedo, T.W., et al., "Structure–Function Analysis of Eotaxin–2/CKbeta–6/MPIF–2," FASEB J. 13:.A317, Abtract No. 252.17, Federation of American Societies for Experimental Biology (Mar. 1999).

```
1   ATGGCAGGCCTGATGACCATAGTAACCAGCCTTCTGTTCCTTGGTGTCTGTGCCACCAC    60
    M  A  G  L  M  T  I  V  T  S  L  L  F  L  G  V  C  A  H  H

61  ATCATCCCTACGGGCTCTGTGGTCATACCCTCTCCCTGCTGCATGTTCTTTGTTCCAAG  120
    I  I  P  T  G  S  V  V  I  P  S  P  C  C  M  F  F  V  S  K

121 AGAATTCCTGAGAACCGAGTGGTCAGTTACCAGCAGTGTCCAGCAGGAGCACATGCCTCAAG  180
    R  I  P  E  N  R  V  V  S  Y  Q  L  S  S  R  S  T  C  L  K

181 GCAGGAGTGATCTTCACCACCAAGAAGGGCCAGCAGTTCTGTGGCGACCCCAAGCAGGAG  240
    A  G  V  I  F  T  T  K  K  G  Q  Q  F  C  G  D  P  K  Q  E

241 TGGGTCCAGAGGTACATGAAGAACCTGGACGCCAAGCAGAAGAAGGCTTCCCCTAGGGCC  300
    W  V  Q  R  Y  M  K  N  L  D  A  K  Q  K  K  A  S  P  R  A

301 AGGGCAGTGGCTGTCAAGGGCCCTGTCCAGAGATATCCTGGCAACCAAACCACCTGCTAA  360
    R  A  V  A  V  K  G  P  V  Q  R  Y  P  G  N  Q  T  T  C  *
```

FIG.1

```
  1  M A G L M T I V T S L L F - L G V C A H H I I P T G S V V I   CP
  1  M K V S A L L C L L L I A A T F I P Q G L A Q P D A I N A    MCP1
  1  M Q V S T A A L A V L L C T M A L C N Q V L S A P L A A D T  MIP1-A

30  P S P C C M F F V S K R I P E N R V V S Y Q L S S R S T C L  CP
 31  P V T C C Y N F T N R K I S V Q R L A S Y R R I T S S K C P  MCP1
 31  P T A C C F S Y T S R Q I P Q N F I A D Y F E - T S S Q C S  MIP1-A

60  K A G V I F T T K Q G Q F C G D P K Q E W V Q R Y M K N L    CP
 61  K E A V I F K T I V A K E I C A D P K Q K W V Q D S M D H L  MCP1
 60  K P S V I F L T K R G R Q V C A D P S E E W V Q K Y V S D L  MIP1-A

90  D A K Q K K A S P R A R A V A V K G P V Q R Y P G N Q T T C  CP
 91  D K Q T Q T P K T                                            MCP1
 90  E L - - - - S A                                              MIP1-A
```

FIG.2

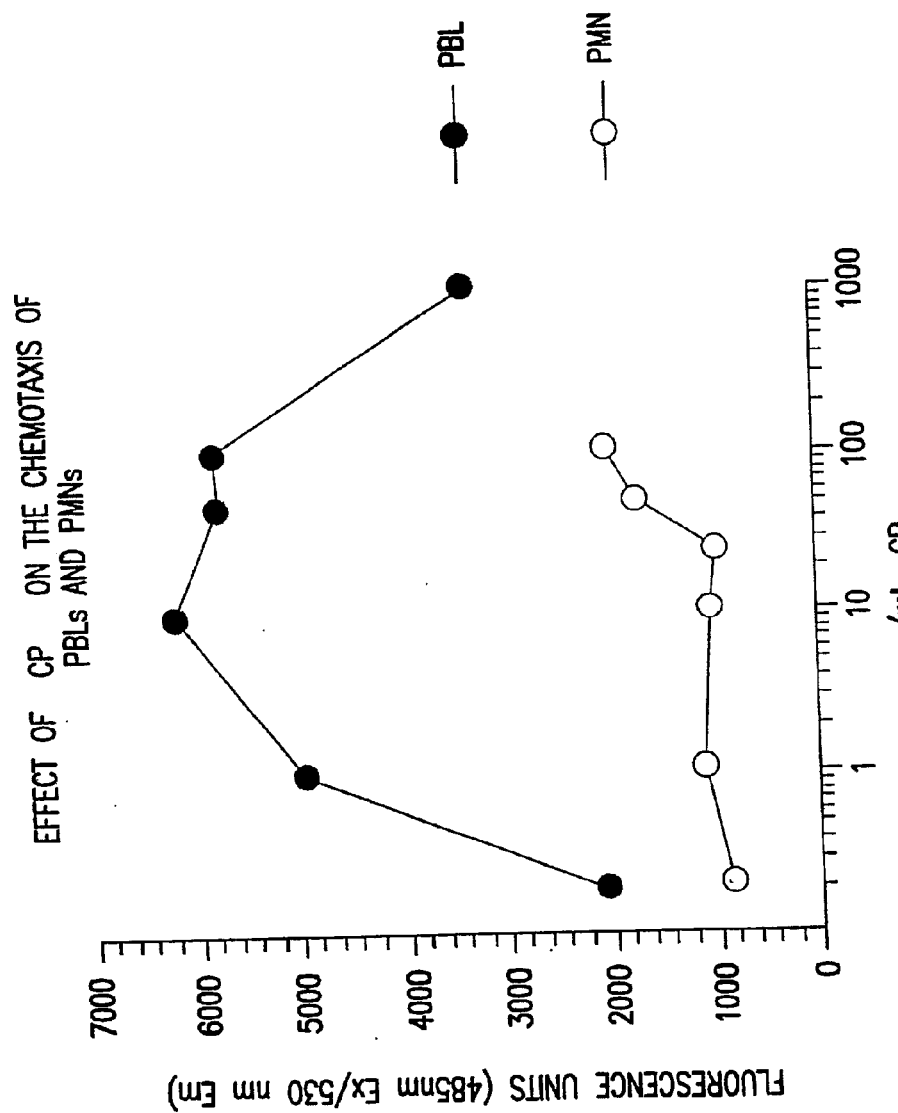

```
                                    -35         Operator 1
 1 AAGCTTAAAAAACTGCAAAAAATAGT TTGACT TGTGAGCGGATAACAAT -10              Operator 2
50 TAAGAT GTACCCA ATTGTGAGCGGATAACAAT TTCACACATTAA

S/D
94 AGAGGAG AAATTA CATATG
```

FIG. 10

```
                         SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..357

(ix) FEATURE:
        (A) NAME/KEY: sig_peptide
        (B) LOCATION: 1..79

(ix) FEATURE:
        (A) NAME/KEY: mat_peptide
        (B) LOCATION: 79..357

(xi) SEQUENCE DESCRIPTION: SEQ ID NO: 1:

ATG GCA GGC CTG ATG ACC ATA GTA ACC AGC CTT CTG TTC CTT GGT GTC      48
Met Ala Gly Leu Met Thr Ile Val Thr Ser Leu Leu Phe Leu Gly Val
-26 -25                 -20                 -15

TGT GCC CAC CAC ATC ATC CCT ACG GGC TCT GTG GTC ATA CCC TCT CCC      96
Cys Ala His His Ile Ile Pro Thr Gly Ser Val Val Ile Pro Ser Pro
-10                 -5                  1                   5

TGC TGC ATG TTC TTT GTT TCC AAG AGA ATT CCT GAG AAC CGA GTG GTC     144
Cys Cys Met Phe Phe Val Ser Lys Arg Ile Pro Glu Asn Arg Val Val
                10                  15                  20

AGC TAC CAG CTG TCC AGC AGG AGC ACA TGC CTC AAG GCA GGA GTG ATC     192
Ser Tyr Gln Leu Ser Ser Arg Ser Thr Cys Leu Lys Ala Gly Val Ile
                25                  30                  35

TTC ACC ACC AAG AAG GGC CAG CAG TTC TGT GGC GAC CCC AAG CAG GAG     240
Phe Thr Thr Lys Lys Gly Gln Gln Phe Cys Gly Asp Pro Lys Gln Glu
        40                  45                  50

TGG GTC CAG AGG TAC ATG AAG AAC CTG GAC GCC AAG CAG AAG AAG GCT     288
Trp Val Gln Arg Tyr Met Lys Asn Leu Asp Ala Lys Gln Lys Lys Ala
55                  60                  65                  70

TCC CCT AGG GCC AGG GCA GTG GCT GTC AAG GGC CCT GTC CAG AGA TAT     336
Ser Pro Arg Ala Arg Ala Val Ala Val Lys Gly Pro Val Gln Arg Tyr
                75                  80                  85
```

```
CCT GGC AAC CAA ACC ACC TGC TAA                                                   360
Pro Gly Asn Gln Thr Thr Cys
            90
```

(2) INFORMATION FOR SEQ ID NO: 2:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Gly Leu Met Thr Ile Val Thr Ser Leu Leu Phe Leu Gly Val
-26 -25         -20              -15

Cys Ala His His Ile Ile Pro Thr Gly Ser Val Val Ile Pro Ser Pro
-10             -5                1              5

Cys Cys Met Phe Phe Val Ser Lys Arg Ile Pro Glu Asn Arg Val Val
             10              15               20

Ser Tyr Gln Leu Ser Ser Arg Ser Thr Cys Leu Lys Ala Gly Val Ile
         25              30              35

Phe Thr Thr Lys Lys Gly Gln Gln Phe Cys Gly Asp Pro Lys Gln Glu
     40              45              50

Trp Val Gln Arg Tyr Met Lys Asn Leu Asp Ala Lys Gln Lys Lys Ala
 55              60              65              70

Ser Pro Arg Ala Arg Ala Val Ala Val Lys Gly Pro Val Gln Arg Tyr
             75              80              85

Pro Gly Asn Gln Thr Thr Cys
            90
```

(2) INFORMATION FOR SEQ ID NO: 3:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

```
TCAGGATCCC CTACGGGCTC GTGGTC                                                       26
```

(2) INFORMATION FOR SEQ ID NO: 4:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 4:

```
TGACCGGCAG CAAAATGAGA TCTCGC                                                       26
```

(2) INFORMATION FOR SEQ ID NO: 5:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO: 5:

Met Lys Val Ser Ala Ala Leu Leu Cys Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr (2) INFORMATION FOR SEQ ID NO: 6:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO: 6:

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90

(2) INFORMATION FOR SEQ ID NO: 7:

(i) SEQUENCE CHARACTERISTICS:
        (A) LENGTH: 3974 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 7:

| | | | | | |
|---|---|---|---|---|---|
| GGTACCTAAG | TGAGTAGGGC | GTCCGATCGA | CGGACGCCTT | TTTTTTGAAT | TCGTAATCAT | 60 |
| GGTCATAGCT | GTTTCCTGTG | TGAAATTGTT | ATCCGCTCAC | AATTCCACAC | AACATACGA | 120 |
| CCGGAAGCAT | AAAGTGTAAA | GCCTGGGGTG | CCTAATGAGT | GAGCTAACTC | ACATTAATT | 180 |
| CGTTGCGCTC | ACTGCCCGCT | TTCCAGTCGG | GAAACCTGTC | GTGCCAGCTG | CATTAATGA | 240 |
| TCGGCCAACG | CGCGGGGAGA | GGCGGTTTGC | GTATTGGGCG | CTCTTCCGCT | TCCTCGCTC | 300 |
| CTGACTCGCT | GCGCTCGGTC | GTTCGGCTGC | GGCGAGCGGT | ATCAGCTCAC | TCAAAGGCG | 360 |
| TAATACGGTT | ATCCACAGAA | TCAGGGGATA | ACGCAGGAAA | GAACATGTGA | GCAAAAGGC | 420 |

| | |
|---|---|
| AGCAAAAGGC CAGGAACCGT AAAAAGGCCG CGTTGCTGGC GTTTTTCCAT AGGCTCCGC | 480 |
| CCCCTGACGA GCATCACAAA ATCGACGCT CAAGTCAGAG GTGGCGAAAC CCGACAGGA | 540 |
| TATAAAGATA CCAGGCGTTT CCCCCTGGAA GCTCCCTCGT GCGCTCTCCT GTTCCGACC | 600 |
| TGCCGCTTAC CGGATACCTG TCCGCCTTTC TCCCTTCGGG AAGCGTGGCG CTTTCTCAT | 660 |
| GCTCACGCTG TAGGTATCTC AGTTCGGTGT AGGTCGTTCG CTCCAAGCTG GGCTGTGTG | 720 |
| ACGAACCCCC CGTTCAGCCC GACCGCTGCG CCTTATCCGG TAACTATCGT CTTGAGTCC | 780 |
| ACCCGGTAAG ACACGACTTA TCGCCACTGG CAGCAGCCAC TGGTAACAGG ATTAGCAGA | 840 |
| CGAGGTATGT AGGCGGTGCT ACAGAGTTCT TGAAGTGGTG GCCTAACTAC GGCTACACT | 900 |
| GAAGAACAGT ATTTGGTATC TGCGCTCTGC TGAAGCCAGT TACCTTCGGA AAAAGAGTT | 960 |
| GTAGCTCTTG ATCCGGCAAA CAAACCACCG CTGGTAGCGG TGGTTTTTTT GTTTGCAA | 1020 |
| AGCAGATTAC GCGCAGAAAA AAGGATCTC AAGAAGATCC TTTGATCTTT TCTACGGG | 1080 |
| CTGACGCTCA GTGGAACGAA AACTCACGTT AAGGGATTTT GGTCATGAGA TTATCGTC | 1140 |
| CAATTCGCGC GCGAAGGCGA AGCGGCATGC ATTTACGTTG ACACCATCGA ATGGTGCA | 1200 |
| ACCTTTCGCG GTATGGCATG ATAGCGCCCG GAAGAGAGTC AATTCAGGGT GGTGAATG | 1260 |
| AAACCAGTAA CGTTATACGA TGTCGCAGAG TATGCCGGTG TCTCTTATCA GACCGTTT | 1320 |
| CGCGTGGTGA ACCAGGCCAG CCACGTTTCT GCGAAAACGC GGGAAAAAGT GGAAGCGG | 1380 |
| ATGGCGGAGC TGAATTACAT TCCCAACCGC GTGGCACAAC AACTGGCGGG CAAACAGT | 1440 |
| TTGCTGATTG GCGTTGCCAC CTCCAGTCTG GCCCTGCACG CGCCGTCGCA AATTGTCG | 1500 |
| GCGATTAAAT CTCGCGCCGA TCAACTGGGT GCCAGCGTGG TGGTGTCGAT GGTAGAAC | 1560 |
| AGCGGCGTCG AAGCCTGTAA AGCGGCGGTG CACAATCTTC TCGCGCAACG CGTCAGTG | 1620 |
| CTGATCATTA ACTATCCGCT GGATGACCAG GATGCCATTG CTGTGGAAGC TGCCTGCA | 1680 |
| AATGTTCCGG CGTTATTTCT TGATGTCTCT GACCAGACAC CCATCAACAG TATTATTT | 1740 |
| TCCCATGAAG ACGGTACGCG ACTGGGCGTG GAGCATCTGG TCGCATTGGG TCACCAGC | 1800 |
| ATCGCGCTGT TAGCGGGCCC ATTAAGTTCT GTCTCGGCGC GTCTGCGTCT GGCTGGCT | 1860 |
| CATAAATATC TCACTCGCAA TCAAATTCAG CCGATAGCGG AACGGGAAGG CGACTGGA | 1920 |
| GCCATGTCCG GTTTTCAACA AACCATGCAA ATGCTGAATG AGGGCATCGT TCCCACTG | 1980 |
| ATGCTGGTTG CCAACGATCA GATGGCGCTG GGCGCAATGC GCGCCATTAC CGAGTCCG | 2040 |
| CTGCGCGTTG GTGCGGATAT CTCGGTAGTG GGATACGACG ATACCGAAGA CAGCTCAT | 2100 |
| TATATCCCGC CGTTAACCAC CATCAAACAG GATTTTCGCC TGCTGGGGCA AACCAGCG | 2160 |
| GACCGCTTGC TGCAACTCTC TCAGGGCCAG GCGGTGAAGG GCAATCAGCT GTTGCCCG | 2220 |
| TCACTGGTGA AAAGAAAAAC CACCCTGGCG CCCAATACGC AAACCGCCTC TCCCCGCG | 2280 |
| TTGGCCGATT CATTAATGCA GCTGGCACGA CAGGTTTCCC GACTGGAAAG CGGGCAGT | 2340 |
| GCGCAACGCA ATTAATGTAA GTTAGCGCGA ATTGTCGACC AAAGCGGCCA TCGTGCCT | 2400 |
| CCACTCCTGC AGTTCGGGGG CATGGATGCG CGGATAGCCG CTGCTGGTTT CCTGGATG | 2460 |
| GACGGATTTG CACTGCCGGT AGAACTCCGC GAGGTCGTCC AGCCTCAGGC AGCAGCTG | 2520 |
| CCAACTCGCG AGGGGATCGA GCCCGGGGTG GGCGAAGAAC TCCAGCATGA GATCCCCG | 2580 |
| CTGGAGGATC ATCCAGCCGG CGTCCCGGAA AACGATTCCG AAGCCCAACC TTTCATAG | 2640 |
| GGCGGCGGTG GAATCGAAAT CTCGTGATGG CAGGTTGGGC GTCGCTTGGT CGGTCATT | 2700 |
| GAACCCCAGA GTCCCGCTCA GAAGAACTCG TCAAGAAGGC GATAGAAGGC GATGCGCT | 2760 |

-continued

```
GAATCGGGAG CGGCGATACC GTAAAGCACG AGGAAGCGGT CAGCCCATTC GCCGCCAA      2820

TCTTCAGCAA TATCACGGGT AGCCAACGCT ATGTCCTGAT AGCGGTCCGC CACACCCA      2880

CGGCCACAGT CGATGAATCC AGAAAAGCGG CCATTTTCCA CCATGATATT CGGCAAGC      2940

GCATCGCCAT GGGTCACGAC GAGATCCTCG CCGTCGGGCA TGCGCGCCTT GAGCCTGG      3000

AACAGTTCGG CTGGCGCGAG CCCCTGATGC TCTTCGTCCA GATCATCCTG ATCGACAA      3060

CCGGCTTCCA TCCGAGTACG TGCTCGCTCG ATGCGATGTT TCGCTTGGTG GTCGAATG      3120

CAGGTAGCCG GATCAAGCGT ATGCAGCCGC CGCATTGCAT CAGCCATGAT GGATACTT      3180

TCGGCAGGAG CAAGGTGAGA TGACAGGAGA TCCTGCCCCG GCACTTCGCC CAATAGCA      3240

CAGTCCCTTC CCGCTTCAGT GACAACGTCG AGCACAGCTG CGCAAGGAAC GCCCGTCG      3300

GCCAGCCACG ATAGCCGCGC TGCCTCGTCC TGCAGTTCAT TCAGGGCACC GGACAGGT      3360

GTCTTGACAA AAAGAACCGG GCGCCCCTGC GCTGACAGCC GGAACACGGC GGCATCAG      3420

CAGCCGATTG TCTGTTGTGC CCAGTCATAG CCGAATAGCC TCTCCACCCA AGCGGCCG      3480

GAACCTGCGT GCAATCCATC TTGTTCAATC ATGCGAAACG ATCCTCATCC TGTCTCTT      3540

TCAGATCTTG ATCCCCTGCG CCATCAGATC CTTGGCGGCA AGAAAGCCAT CCAGTTTA      3600

TTGCAGGGCT TCCCAACCTT ACCAGAGGGC GCCCCAGCTG GCAATTCCGG TTCGCTTG      3660

GTCCATAAAA CCGCCCAGTC TAGCTATCGC CATGTAAGCC CACTGCAAGC TACCTGCT      3720

CTCTTTGCGC TTGCGTTTTC CCTTGTCCAG ATAGCCCAGT AGCTGACATT CATCCGGG      3780

CAGCACCGTT TCTGCGGACT GGCTTTCTAC GTGTTCCGCT TCCTTTAGCA GCCCTTGC      3840

CCTGAGTGCT TGCGGCAGCG TGAAGCTTAA AAAACTGCAA AAAATAGTTT GACTTGTG      3900

CGGATAACAA TTAAGATGTA CCCAATTGTG AGCGGATAAC AATTTCACAC ATTAAAGA      3960

AGAAATTACA TATG                                                     3974
```

(2) INFORMATION FOR SEQ ID NO: 8:

(i) SEQUENCE CHARACTERISTICS:
        (A) LENGTH: 112 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 8:

```
AAGCTTAAAA AACTGCAAAA AATAGTTTGA CTTGTGAGCG GATAACAATT AAGATGTACC      60

CAATTGTGAG CGGATAACAA TTTCACACAT TAAAGAGGAG AAATTACATA TG              112
```

ANTIBODIES TO HUMAN CHEMOTACTIC PROTEIN

This application is a division of application Ser. No. 09/453,416, filed Dec. 3, 1999 (now U.S. Pat. No. 6,419,917, issued Jul. 16, 2002) which is a division of application Ser. No. 09/044,855, filed Mar. 20, 1998 (now U.S. Pat. No. 6,100,389, issued Aug. 8, 2000) which is a continuation-in-part of application Ser. No. 08/479,126, filed Jun. 7, 1995, (now U.S. Pat. No. 5,866,373, issued Feb. 2, 1999) which is a continuation-in-part of application Ser. No. 08/424,425, filed Apr. 21, 1995, (now abandoned) and International Application No. PCT/US94/05384, filed May 16, 1994, each of which disclosure is herein incorporated by reference.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a chemotactic protein. The invention also relates to inhibiting the action of such polypeptides.

RELATED ART

There are three forms of monocyte chemotactic protein, namely, MCP-1, MCP-2 and MCP-3. All of these proteins have been structurally and functionally characterized and have also been cloned and expressed. MCP-1 and MCP-2 have the ability to attract leukocytes (monocytes, and leukocytes), while MCP-3 also attracts eosinophils and T lymphocytes (Dahinderi, E. et al., J. Exp. Med., 179:751–756 (1994)).

Initially, human monocyte-specific attracting factor, was purified from a glioma cell line and a monocytic cell line. Matsushima, K. et al, J. Exp. Med., 169:1485–1490 (1989). This factor was originally designated glioma-derived chemotactic factor (GDCF) and monocyte chemotactic and activating factor (MCAF) by Matsushima, et al. This factor is now referred to as MCP-1. Subsequent cloning of the cDNA for MCP-1 showed it to be highly similar to the murine JE gene. The JE gene could be massively induced in murine fibroblasts by platelet-derived growth factor. Cochran, B. H., et al, Cell 33:939–947 (1983). Murine JE is highly similar to MCP-1. The MCP-1 protein is 62% identical to murine JE in a region of 68 shared N-terminal residues. It is widely accepted that JE and MCP-1 are species homologs.

A method of suppressing tumor formation in a vertebrate by administering JE/MCP-1 has been disclosed in PCT application WO-92/20372, along with methods of treating localized complications of malignancies and methods of combatting parasitic infection by administering JE/MCP-1. Expression of the JE/MCP-1 protein in malignant cells was found to suppress the cells ability to form tumors in vivo.

Human MCP-1 is a basic peptide of 76 amino acids with a predicted molecular mass of 8,700 daltons. MCP-1 is inducibly expressed mainly in monocytes, endothelial cells and fibroblasts. Leonard, E. J. and Yoshimura, T., Immunol. Today, 11:97–101 (1990). The factors which induce this expression is IL-1, TNF or lipopolysaccharide treatment.

Other properties of MCP-1 include the ability to strongly activate mature human basophils in a pertussis toxin-sensitive manner. MCP-1 is a cytokine capable of directly inducing histamine release by basophils, (Bischoff, S. C. et al., J. Exp. Med., 175:1271–1275 (1992)). Furthermore, MCP-1 promotes the formation of leukotriene C4 by basophils pretreated with Interleukin 3, Interleukin-5, or granulocyte/macrophage colony-stimulating factor. MCP-1 induced basophil mediator release may play an important role in allergic inflammation and other pathologies expressing MCP-1.

Clones having a nucleotide sequence encoding a human monocyte chemotactic and activating factor (MCAF) reveal the primary structure of the MCAF polypeptide to be composed of a putative signal peptide sequence of 23 amino acid residues and a mature MCAF sequence of 76 amino acid residues. Furutani, Y. H., et al, Biochem. Biophys. Res. Commu., 159:249–55 (1989). The complete amino acid sequence of human glioma-derived monocyte chemotactic factor (GDCF-2) has also been determined. This peptide attracts human monocytes but not neutrophils. It was established that GDCF-2 comprises 76 amino acid residues. The peptide chain contains 4 half-cysteines, at positions 11, 12, 36 and 52, which create a pair of loops, clustered at the disulfide bridges. Further, the MCP-1 gene has been designated to human chromosome 17. Mehrabian, M. R., et al, Genomics, 9:200–3 (1991). Certain data suggests that a potential role for MCP-1 is mediating monocytic infiltration of the artery wall. Monocytes appear to be central to atherogenesis both as the progenitors of foam cells and as a potential source of growth factors mediating intimal hyperplasia. Nelken, N. A., et al, J. Clin. Invest., 88:1121–7 (1991). It has also been found that synovial production of MCP-1 may play an important role in the recruitment of mononuclear phagocytes during inflammation associated with rheumatoid arthritis and that synovial tissue macrophages are the dominant source of this cytokine. MCP-1 levels were found to be significantly higher in synovial fluid from rheumatoid arthritis patients compared to synovial fluid from osteoarthritis patients or from patients with other arthritides. Koch, A. E., et al, J. Clin. Invest., 90:772–9 (1992).

MCP-2 and MCP-3 are classified in a subfamily of proinflammatory proteins and are functionally related to MCP-1 because they specifically attract monocytes, but not neutrophils. Van Damme, J., et al, J. Exp. Med., 176:59–65 (1992). MCP-3 shows 71% and 58% amino acid homology to MCP-1 and MCP-2 respectively. MCP-3 is an inflammatory cytokine that regulates macrophage functions.

The transplantation of hemolymphopoietic stem cells has been proposed in the treatment of cancer and hematological disorders. Many studies demonstrate that transplantation of hematopoietic stem cells harvested from the peripheral blood have advantages over the transplantation of marrow-derived stem cells. Due to the low number of circulating stem cells, there is a need for induction of pluripotent marrow stem cell mobilization into the peripheral blood. Reducing the amount of blood to be processed to obtain an adequate amount of stem cells would increase the use of autotransplantation procedures and eliminate the risk of graph versus host reaction connected with allotransplantation. Presently, blood mobilization of marrow CD34$^+$ stem cells is obtained by the injection of a combination of agents, including antiblastic drugs and G-CSF or GM-CSF. Drugs which are capable of stem cell mobilization include IL-1, IL-7, IL-8, and NIP-1α. Both IL-1 and IL-8 demonstrate proinflammatory activity that may be dangerous for good engrafting. IL-7 must be administered at high doses over a long duration and MIP-1α is not very active as a single agent and shows best activity when in combination with G-CSF.

SUMMARY OF THE INVENTION

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, for stem cell mobilization, myeloprotection and neuronal protection, to treat tumors, to promote wound healing, to combat parasitic infection and to regulate hematopoiesis.

In accordance with yet a further aspect of the present invention, there are provided antibodies against such polypeptides.

In accordance with another aspect of the present invention, there are provided agonists which mimic the polypeptide of the present invention and bind to receptors to elicit second messenger responses.

In accordance with yet another aspect of the present invention, there are provided antagonists to such polypeptides, which may be used to inhibit the action of such polypeptides, for example, in the treatment of rheumatoid arthritis, lung inflammation, allergy, infectious diseases and to prevent inflammation and atherosclerosis.

In accordance with yet a further aspect of the present invention, there is also provided nucleic acid probes comprising nucleic acid molecules of sufficient length to specifically hybridize to a nucleic acid sequence of the present invention.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIG. 1 depicts the cDNA (SEQ ID NO:1) sequence and corresponding deduced amino acid sequence (SEQ ID NO:2) of a chemotactic protein of the present invention (CP). The 119 amino acid sequence shown is the full length protein, with approximately the first 26 amino acids representing a leader sequence (underlined) such that the mature form of the protein is 93 amino acids in length. The standard one letter abbreviation for amino acids is used.

FIG. 2 illustrates a comparison of the amino acid sequence homology between the polypeptide of the present invention (SEQ ID NO:2), MCP-1 (SEQ ID NO:5) and MIP-1α (SEQ ID NO:6). The polypeptide of the present invention (CP) shows 39% homology with MIP-1α and 34% homology with MCP-1.

FIG. 3 illustrates the chemotactic activity of the polypeptide of the present invention on neutrophils (PMN) and peripheral blood leukocytes (PBL). Neutrophils and peripheral blood leukocytes were isolated from peripheral blood, loaded with calcein-AM and used for chemotaxis in a 96 well, single-use Neuroprobe chemotactic chamber. After 90 minutes incubation with the polypeptide of the present invention (CP), the chamber was dismounted, the filter air-dried and the number of cells which migrated through the membrane quantitated in a cytofluor II.

FIG. 10 shows the nucleotide sequence of the regulatory elements of the pHE4a promoter (SEQ ID NO:8). The two lac operator sequences, the Shine-Delgarno sequence (S/D), and the terminal HindIII and NdeI restriction sites (italicized) are indicated.

DETAILED DESCRIPTION OF THE INVENTION

Figure 4A:
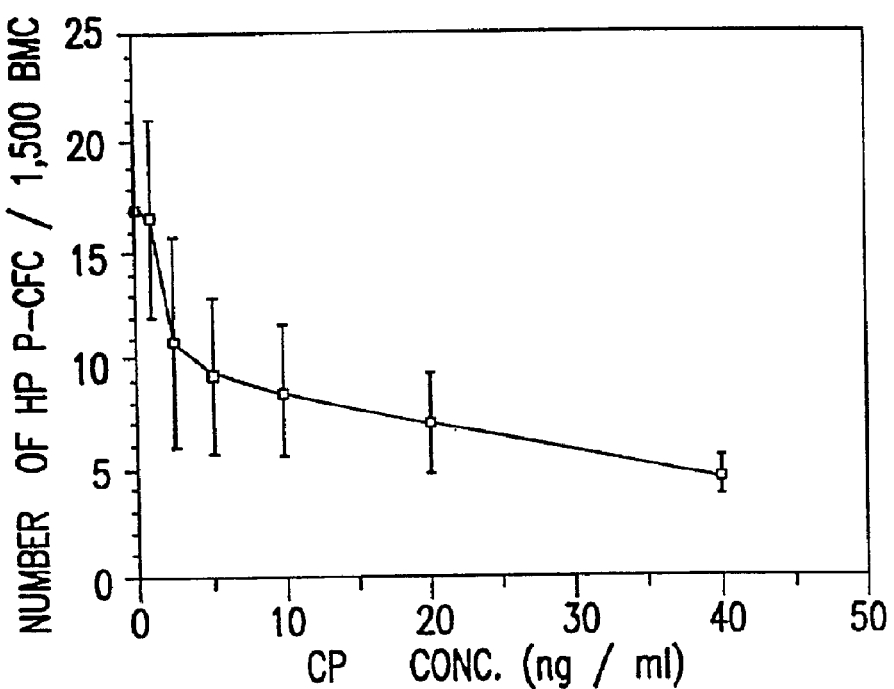
FIGS. 4A–4B illustrate that the polypeptide of the present invention (CP) inhibits the growth and differentiation of high proliferative potential colony forming cells (HPP-CFC) (A) and is not effective on low proliferative potential colony forming cells (LPP-CFC) (B). In these experiments, 1,500 cells from low density, non-adherent bone marrow cells were plated in agar-medium supplemented with 5 ng/ml mouse IL-3, 100 ng/ml mouse SCF, 10 ng/ml mouse IL-1α, 5 ng/ml human M-CSF, and with or without the indicated concentrations of the polypeptide of the present invention (CP). Colonies were scored after 14 days of incubation. Three experiments were performed. The results are presented as mean number of colonies ±SD. An irrelevant protein had no effects.

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited at the American Type Culture Collection, (ATCC) 10801 University Boulevard, Manassas, Va. 20110-2209 (present address), as ATCC Deposit No. 75703 on Mar. 10, 1994.

The polynucleotide of this invention was discovered from an activated monocyte cDNA library. It contains an open reading frame encoding a protein of approximately 119-amino acids in length of which the first 26 amino residues comprise a putative leader sequence. The mature protein therefore is predicted to be 93 amino acids in length. It is structurally related to mouse monocyte chemotactic protein (MCP-1 or JE), showing 27identity, and 56% similarity over the entire human MCP-1 protein sequence. The polypeptide contains all four cysteine residues that occur in all chemokines in a characteristic motif. The spacing between these cysteines is conserved compared with the murine MCP-1J/E which strongly suggests that the new gene is a chemokine.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as $E.$ $coli,$ $Streptomyces,$ $Salmonella$ $typhimurium;$ fungal cells, such as yeast; insect cells such as $Drosophila$ S2 and $Spodoptera$ Sf9; animal cells such as CHO, COS or Bowes melanoma; adenoviruses; plant cells, etc. The selection of an appropriate host is deemed to be within the scope of those skilled in the art from the teachings herein.

In addition to the use of expression vectors in the practice of the present invention, the present invention further includes novel expression vectors comprising operator and promoter elements operatively linked to nucleotide sequences encoding a protein of interest. One example of such a vector is pHE4a which is described in detail below.

Figure 9:
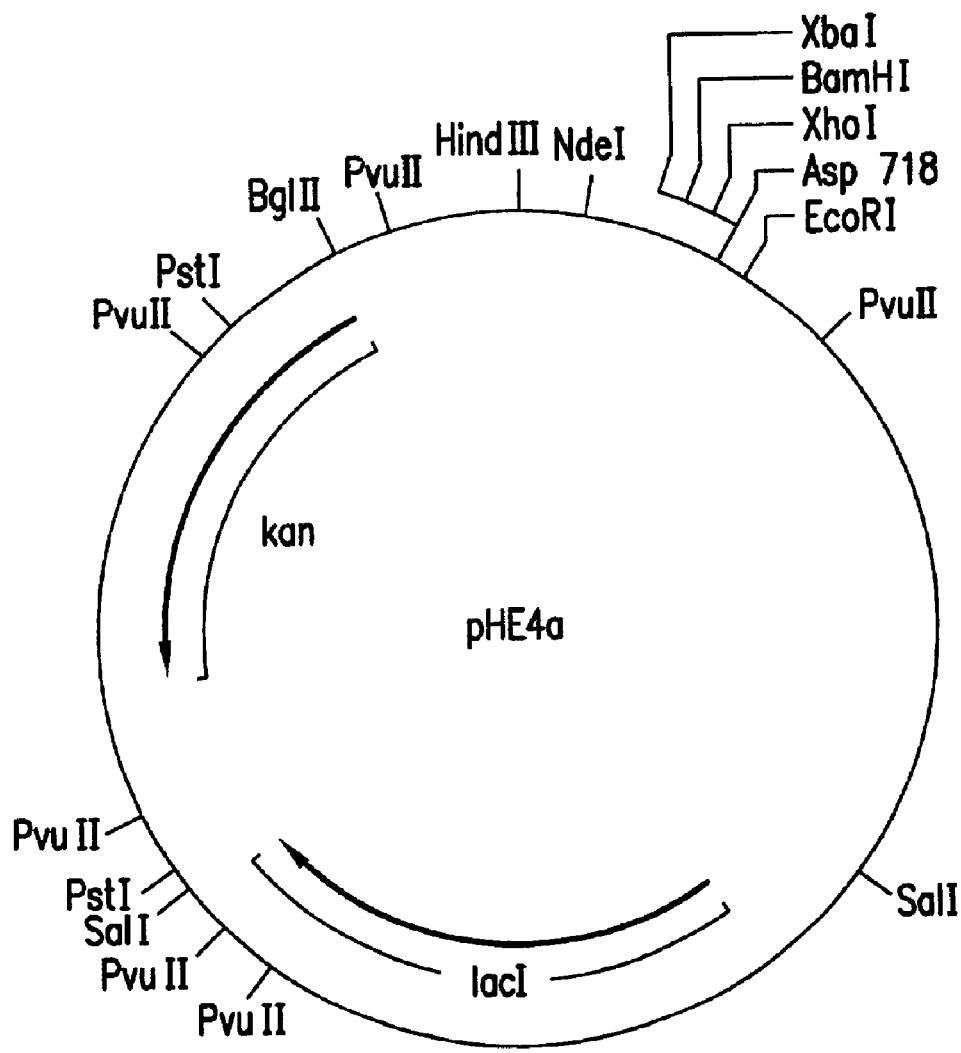
FIG. 9 shows a schematic representation of the pHE4a expression vector (SEQ ID NO:7). The locations of the kanamycin resistance marker gene, the multiple cloning site linker region, the oriC sequence, and the lacIq coding sequence are indicated.

As summarized in FIGS. 9 and 10, components of the pHE4a vector (SEQ ID NO:7) include: 1) a neomycinphosphotransferase gene as a selection marker, 2) an $E.$ $coli$ origin of replication, 3) a T5 phage promoter sequence, 4) two lac operator sequences, 5) a Shine-Delgarno sequence, 6) the lactose operon repressor gene (lacIq) and 7) a multiple cloning site linker region. The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. The pHE4a vector was deposited with the ATCC on Feb. 25, 1998, and given accession number 209645.

A nucleotide sequence encoding the polypeptide of the present invention (CP) (SEQ ID NO:1), is operatively linked to the promoter and operator of pHE4a by restricting the vector with NdeI and either XbaI, BamHI, XhoI, or Asp718, and isolating the larger fragment (the multiple cloning site region is about 310 nucleotides) on a gel. The nucleotide sequence encoding the polypeptide of the present invention (CP) (SEQ ID NO:1) having the appropriate restriction sites is generated, for example, according to the PCR protocol described in Example 1, using PCR primers having restriction sites for NdeI (as the 5' primer) and either XbaI, BamHI, XhoI, or Asp718 (as the 3' primer). The PCR insert is gel purified and restricted with compatible enzymes. The insert and vector are ligated according to standard protocols.

As noted above, the pHE4a vector contains a lacIq gene. LacIq is an allele of the lacI gene which confers tight regulation of the lac operator. Amann, E. et al., $Gene$ 69:301–315 (1988); Stark, M. , $Gene$ 51:255–267 (1987). The lacIq gene encodes a repressor protein which binds to lac operator sequences and blocks transcription of downstream (i.e., 3') sequences. However, the lacIq gene product dissociates from the lac operator in the presence of either lactose or certain lactose analogs, e.g., isopropyl B-D-thiogalactopyranoside (IPTG). The polypeptide of the present invention (CP) thus is not produced in appreciable quantities in uninduced host cells containing the pHE4a vector. Induction of these host cells by the addition of an agent such as IPTG, however, results in the expression of the CP coding sequence.

The promoter/operator sequences of the pHE4a vector (SEQ ID NO:8) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., $TEXTBOOK$ $OF$ $BIOCHEMISTRY$ $WITH$ $CLINICAL$ $CORRELATIONS$, 4th Edition (1997), pages 802–807.

The pHE4 series of vectors contain all of the components of the pHE4a vector except for the CP coding sequence. Features of the pHE4a vectors include optimized synthetic T5 phage promoter, lac operator, and Shine-Delagarno sequences. Further, these sequences are also optimally spaced so that expression of an inserted gene may be tightly regulated and high level of expression occurs upon induction.

Among known bacterial promoters suitable for use in the production of proteins of the present invention include the $E.$ $coli$ lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4a vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4a vector (SEQ ID NO:7).

The present invention further includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polypeptide of the present invention (CP), may be employed for the promotion of wound healing. Since CP is a chemokine, it is a chemo-attractant for leukocytes (such as basophils, PMNs, PBLs (peripheral blood leukocytes). etc.); therefore, it causes infiltration of target immune cells to a wound area.

The polypeptide of the present invention (CP) may also be employed as an anti-tumor treatment and for treating localized complications of a malignancy, such as pleural effusions or ascites.

The presence of MCPs in vivo is accompanied by a local increase in the presence of eosinophils which have the distinctive function of killing the larvae of parasites that invade tissues, as in schistosomiasis, trichinosis and ascariasis. Therefore, the polypeptide of the present invention (CP) may be employed for combatting parasitic infections.

The polypeptide of the present invention may be employed for mobilizing hematopoietic progenitor cells into the peripheral blood circulation of a non-human and human host, preferably a human host, for subsequent recovery and use thereof in transplantation. The polypeptide of the present invention is administered in an amount effective to mobilize into and increase the amount of hematopoietic progenitor cells in the peripheral blood, in particular, increase the amount of human hematopoietic stem cells in the peripheral blood. Such cells are often referred to as CD34+ cells. For example, the polypeptide is administered in amounts as hereinafter described. The polypeptide of the present invention may be administered alone or in conjunction with other agents, for example, GM-CSF and G-CSF which are known to be effective for increasing such cells in peripheral blood. Mobilization of hematopoietic progenitor cells into the peripheral circulation is important for autologous and heterologous bone marrow transfers which are used, for example for treatment of cancer and hematological disorders.

The polypeptide of the present invention may also be employed to inhibit destruction of hematopoietic progenitor cells in a non-human and human host, preferably a human host, resulting from treatment with chemotherapeutic agents. The polypeptide of the present invention may be administered prior to, during or subsequent to chemotherapy and allows a higher dose of chemotherapy to be employed in the treatment of cancer. The polypeptide of the present invention is administered in an amount effective to inhibit destruction of hematopoietic progenitor cells; for example, the polypeptide is administered in amounts as hereinafter described. The polypeptide may be administered alone or in conjunction with other agents. The polypeptide of the present invention may also be employed to protect hematopoietic progenitor cells to thereby prevent or inhibit diseases which may result from the destruction thereof; for example, leukopenia, myelo-dysplastic syndrome, and neutropenia.

The polypeptide of the present invention may also be employed in amounts effective to inhibit the degeneration of neuronal cells in non-human and human hosts, preferably a human host, which results from neuronal degenerative dieases such as Alzheimer's disease, Parkinson's disease and AIDS-related complex. For example, the polypeptide may be employed in amounts as hereinafter described.

TABLE 1

Effect of CP administration to mice on the distribution of the primitive hematopoietic progenitors in peripheral blood, spleen, and bone marrow after two days

| Treatment | $10^4$ PB cells | | Numbers of Progenitors per $10^4$ Spleen cells | | | | $10^4$ BM cells | |
|---|---|---|---|---|---|---|---|---|
| | HPP | LPP | IM | HPP | LPP | IM | HPP | LPP |
| Saline | 0.5 ± 0.7 | 38 ± 9.5 | 6.5 ± 1.9 | 0.7 ± 1.5 | 5.5 ± 2.5 | 1.5 ± 2.3 | 53 ± 11 | 484 ± 59 |
| CP (1 mg/kg/day) | 3.5 ± 0.5 | 95 ± 16.9 | 25 ± 13.5 | 2.75 ± 0.9 | 4.2 ± 3.5 | 3.5 ± 2.4 | 27 ± 3.5 | 610 ± 28 |

PB = Peripheral blood, mononuclear cells
Spl. = Low density fraction of spleen cells
BM = Bone marrow fraction that is 6-fold enriched for the primitive cells
HPP = High proliferative potential colony forming cells
LPP = Low proliferative potential colony forming cells
IM = Immature cell, a rare cell type found in the bone marrow, gives rise to a highly refractile, small (<50 cells/ colony) colony in the presence of multiple cytokines; the cells within the colony are stacked in a horizontal plane and they exhibit blast cell like nuclear staining characteristics.

TABLE 1-continued

Effect of CP administration to mice on the distribution of the primitive hematopoietic progenitors in peripheral blood, spleen, and bone marrow after two days

| | $10^4$ PB cells | | Numbers of Progenitors per $10^4$ Spleen cells | | | $10^4$ BM cells | |
|---|---|---|---|---|---|---|---|
| Treatment | HPP | LPP | IM | HPP | LPP | IM | HPP | LPP |

Three mice were injected IP daily with either the polypeptide of the present invention (CP) or saline. Forty eight hours after the first injection, blood was collected from each animal by cardiac puncture and mice were then sacrificed to obtain bone marrow and spleen. Indicated numbers of cells from each of the tissues were then plated in duplicates in agar-containing medium in the presence of rmIL-3 (5 ng/ml), rmSCF (50 ng/ml), rhM-CSF (5 ng/ml), and rmIL-1a (10 ng/ml) and incubated for 14 days. Data are pooled from three animals in each group and expressed as mean ± S.D.

TABLE 2

Effect of CP administration to mice on the distribution of the primitive hematopoietic progenitors in peripheral blood, spleen, and bone marrow after four days

| | $10^4$ PB cells | | Numbers of Progenitors per $10^4$ Spleen cells | | | | $10^4$ BM cells | |
|---|---|---|---|---|---|---|---|---|
| Treatment | HPP | LPP | IM | HPP | LPP | IM | HPP | LPP |
| Saline | 0 | 29 ± 5.6 | 1 ± 1.5 | 1 ± 0.6 | 10 ± 4.6 | 0.8 ± 0.7 | 60 ± 8 | 505 ± 45 |
| CP (1 mg/kg/day) | 3.8 ± 1.5 | 84.5 ± 14.5 | 28.6 ± 8.6 | 2.6 ± 0.5 | 10.3 ± 2.1 | 7 ± 1.5 | 26.5 ± 8 | 330 ± 46 |

PB = Peripheral blood, mononuclear cells
Spl. = Low density fraction of spleen cells
BM = Bone marrow fraction that is 6-fold enriched for the primitive cells
HPP = High proliferative potential colony forming cells
LPP = Low proliferative potential colony forming cells
IM = Immature cell, a rare cell type found in the bone marrow, gives rise to a highly refractile, small (<50 cells/colony) colony in the presence of multiple cytokines; the cells within the colony are stacked in a horizontal plane and they exhibit blast cell like nuclear staining characteristics.
Three mice were injected IP daily with either the the polypeptide of the present invention (CP) or saline. Ninety six hours after the first injection, blood was collected from each animal by cardiac puncture and mice were then sacrificed to obtain bone marrow and spleen. Indicated numbers of cells from each of the tissues were then plated in duplicates in agar-containing medium in the presence of rmIL-3 (5 ng/ml), rmSCF (50 ng/ml), rhM-CSF (5 ng/ml), and rmIL-1a (10 ng/ml) and incubated for 14 days. Data are pooled from three animals in each group and expressed as mean ± S.D.

TABLE 3

Analysis of the peripheral blood leukocyte composition by FACSan in mice administered with CP after two days

| | Percent Positive in the Gated the Cell Populations | | | | |
|---|---|---|---|---|---|
| Treatment | CD45R+ B-Cells | GR.1+ PMN | Mac. 1+ Monocytes | CD8+ T-cells | CD4+ T-cells |
| Saline | 40.5 ± 9.2 | 62.5 ± 10.6 | 19.5 ± 2.1 | 29 ± 5.6 | 39 ± 12 |
| CP (mg/Kg/day) | 37 ± 5.6 | 56 ± 11.3 | 18 ± 4.2 | 27 ± 4.3 | 33 ± 7 |

Three C57 Black 6 mice (~20 g weight) were injected (IP) daily with either saline or the polypeptide of the present invention (CP). Forty eight hours after the first injection, blood was collected by cardiac puncture and mice were sacrificed to obtain spleen and bone marrow cells. For immunostaining, 0.1 ml of blood from each of the animal was first treated with Gen Trak lysing solution to lyse the red blood cells. Nucleated cells were then sedimented, washed with PBS, and incubated with PE-conjugated monoclonal antibodies against CD45R, Gr. 1, Mac. 1, CD4, & CD8 and processed for flowcytometry. At least 10,000 cells were analyzed. Data are expressed as mean percent positive cells in the appropriate channels ± SD.

The polynucleotides and polypeptides of the present invention may be employed as research reagents and materials for discovery of treatments and diagnostics to human disease.

This invention provides a method for identification of the receptor for the polypeptide of the present invention (CP). The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the polypeptide of the present invention (CP), and a cDNA library created from this RNA is divided into pools and used to transfect COS cells or other cells that are not responsive to CP. Transfected cells which are grown on glass slides are exposed to labeled polypeptide of the present invention (CP). The polypeptide of the present invention (CP) can be labeled by a variety of means including iodination or inclusion of a recognition site for a site-specific protein kinase. Following fixation and incubation, the slides are subjected to auto-radiographic analysis. Positive pools are identified and sub-pools are prepared and re-transfected using an iterative sub-pooling and re-screening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention also provides a method of screening compounds to identify agonists and antagonists to the polypeptide of the present invention. As an example, a mammalian cell or membrane preparation expressing a CP receptor would be contacted with a compound of interest. The ability of the compound to generate a response of a known second messenger system following interaction with the CP receptor is then measured. Such second messenger systems include but are not limited to, cAMP guanylate cyclase, ion channels or phosphoinositide hydrolysis. The ability of a compound to bind the CP receptor and elicit a second messenger response identifies that compound as an agonist. A compound which binds but does not elicit a second messenger response identifies that compound as an antagonist.

A competitive binding assay, in which the compounds are labeled, for example by radioactivity may also be employed to identify antagonists. Such methods are known in the art.

Antagonists include negative dominant mutants of the polypeptide of the present invention (CP). The polypeptide of the present invention (CP) is a tetrameric polypeptide wherein one mutated unit will cause the entire polypeptide to be non-functional. A negative dominant mutant of the polypeptide of the present invention (CP) binds to the CP receptor but fails to activate cells (leukocytes) to which it binds. An assay to detect negative dominant mutants of the polypeptide of the present invention (CP) is an in vitro chemotaxis assay wherein a multiwell chemotaxis chamber equipped with polyvinylpyrrolidone-free polycarbonate membranes is used to measure the chemoattractant ability of the polypeptide of the present invention (CP) for leukocytes in the presence and absence of potential antagonist or agonist molecules.

Potential antagonists also include an antibody, or in some cases, an oligopeptide, which binds to the polypeptide and prevents it from binding its receptor.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of the polypeptide of the present invention (CP). The antisense RNA oligonucleotide hybridizes to the mRNA in vivo and blocks translation of the mRNA molecule into the polypeptide of the present invention (CP)(Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the polypeptide of the present invention (CP).

Potential antagonists include a small molecule which binds to and occupies the active site of the polypeptide thereby making the catalytic site inaccessible to substrate such that normal biological activity is prevented. Examples of small molecules include but are not limited to small peptides or peptide like molecules.

The antagonists may be employed to treat inflammation by preventing the attraction of monocytes to a wound or a site of trauma, and to regulate normal pulmonary macrophage populations, since acute and chronic inflammatory pulmonary diseases are associated with sequestration of mononuclear phagocytes in the lung.

The antagonists may be employed in a composition with a pharmaceutically acceptable carrier, e.g., as hereinabove described.

The polypeptides, and agonists and antagonists, of the present invention may be employed in combination with a suitable pharmaceutical carrier. Such compositions comprise a therapeutically effective amount of the polypeptide or agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides, or agonists and antagonists, of the present invention may be employed in conjunction with other therapeutic compounds.

The pharmaceutical compositions may be administered in a convenient manner such as by the oral, topical, parenterally, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of the polypeptide of the present invention (CP).

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the polypeptide of the present invention (CP) can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples can detect the presence of the polypeptide of the present invention (CP). Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the CP antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention (CP) are attached to a solid support and labeled CP and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLES

Example 1
Bacterial Expression and Purification of CP

The DNA sequence encoding for the polypeptide of the present invention (CP), ATCC #75703, is initially amplified using PCR oligonucleotide primers corresponding to the 5' and 3' sequences of the processed CP protein (minus the signal peptide sequence) and the vector sequences 3' to the CP gene. Additional nucleotides corresponding to CP were added to the 5' and 3' sequences respectively. The 5' oligonucleotide primer has the sequence 5' TCAGGATC-CCCTACGGGCTCGTGGTC 3' (SEQ ID NO:3) contains a Bam H1 restriction enzyme site followed by 18 nucleotides of CP coding sequence starting from the presumed terminal amino acid of the processed protein codon. The 3' sequence 3' CGCTCTAGAGTAAAACGACGGCCAGT 5' (SEQ ID NO:4) contains complementary sequences to the XbaI site and to a pBluescript SK– vector sequence located 3' to the CP DNA insert. The restriction enzyme sites correspond to the restriction enzyme sites on the bacterial expression vector pQE-9. (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with Bam H1 and Xba I. The amplified sequences were ligated into pQE-9 and were inserted in frame with the sequence encoding for the histidine tag and the RBS. The ligation mixture was then used to transform E. coli strain m15/rep4 available from Qiagen under the trademark M15/rep 4 by the procedure described in Sambrook, J. et al, Molecular Cloning: A Laboratory Manual, Cold Spring Laboratory Press, 1989. M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HC1. After clarification, solubilized polypeptide of the present invention (CP) was purified from this solution by chromatography on a Nickel-Chelate column under conditions that allow for tight binding by proteins containing the 6-His tag. Hochuli, E. et al., J. Chromatography 411:177–184 (1984). The polypeptide of the present invention (CP) (95% pure) was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

Example 2
Expression Pattern of CP in Human Cells

Northern blot analysis was carried out to examine the levels of expression of the polypeptide of the present invention (CP) in human cells. Total cellular RNA samples were isolated with RNAzol™ B system (Biotecx Laboratories, Inc. 6023 South Loop East, Houston, Tex. 77033). About 10 μg of total RNA isolated from each human tissue specified was separated on 1% agarose gel and blotted onto a nylon filter. (Sambrook, Fritsch, and Maniatis, Molecular Cloning, Cold Spring Harbor Press, (1989)). The labeling reaction was done according to the Stratagene Prime-It kit with 50ng DNA fragment. The labeled DNA was purified with a Select-G-50 column. (5 Prime-3 Prime, Inc. 5603 Arapahoe Road, Boulder, Colo. 80303). The filter was then hybridized with radioactive labeled full length CP gene at 1,000,000 cpm/ml in 0.5 M $NaPO_4$, pH 7.4 and 7% SDS overnight at 65° C. After washing twice at room temperature and twice at 60° C. with 0.5×SSC, 0.1% SDS, the filter was then exposed at −70° C. overnight with an intensifying screen. The message RNA for CP is abundant in activated and unactivated T cells, monocytes and T cell lines.

Example 3

Cloning and Expression of CP using the Baculovirus Expression System

The DNA sequence encoding the full length polypeptide of the present invention (CP) protein, ATCC #75703, is amplified using PCR oligonucleotide primers corresponding to the 5' and 3' sequences of the gene:

The amplified sequences were isolated from a 1% agarose gel using a commercially available kit ("Geneclean," BIO 101 Inc., La Jolla, Calif.). The fragment was then digested with restriction endonucleases corresponding to the amplified products and then purified again on a 1% agarose gel. This fragment is designated F2.

The vector pRG1 (modification of pVL941 vector, discussed below) is used for the expression of the polypeptide of the present invention (CP) using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases used to digest the amplified products. The polyadenylation site of the simian virus (SV)40 is used for efficient polyadenylation. For an easy selection of recombinant virus the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes and dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. E.coli HB101 cells are then transformed and bacteria identified that contained the plasmid (pBacCP) with the CP gene using the enzymes. The sequence of the cloned fragment is confirmed by DNA sequencing.

5 µg of the plasmid pBacCP is co-transfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBacCP are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate was put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus is added to the cells, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-CP at a multiplicity of infection (MOI) of 2. Six hours later the medium is removed and replaced with SF900 II medium minus methionine and cysteine (Life Technologies Inc., Gaithersburg). 42 hours later 5 µCi of $^{35}S$-methionine and 5 µCi $^{35}S$ cysteine (Amersham) are added. The cells are further incubated for 16 hours before they are harvested by centrifugation and the labeled proteins visualized by SDS-PAGE and autoradiography.

Example 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer further includes a HindIII site. Equal quantities of the Moloney murine sarcoma virus linear backbone and the amplified EcoRI and HindIII fragment are added together, in the presence of T4 DNA ligase.

The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Example 5
Primary Indication of CP as a Mobilizer of Marrow Stem Cells (Bone Marrow Rescue)

The effect of the polypeptide of the present invention (CP) on the distribution of the primitive hematopoietic progenitors in peripheral blood, spleen, and bone marrow was studied in 16 week old C57B1/6 mice (about 20 g). In the first experiment, 3 mice were injected i.p. daily with 1 mg/kg the polypeptide of the present invention (CP) or saline for 2 days and analyzed 24 hours after the last injection. In the second experiment, another 3 mice were injected i.p. daily with 1 mg/kg the polypeptide of the present invention (CP) or saline for 4 days and analyzed 24 hours after the last injection. In both the experiments, the blood of each animal was collected by cardiac puncture and the mice were sacrificed to obtain bone marrow and spleens. The indicated number of cells from each of the tissues was then plated in duplicates in agar-containing medium in the presence of 5 ng/ml IL-3, 50 ng/ml SCF, 5 ng/ml M-CSF and 10 ng/ml IL-1α and incubated for 14 days. In the 2 experiments, the data from the different animals were pooled and expressed as mean±S.D. The results of both experiments shows that the polypeptide of the present invention (CP) mobilizes stem cells from bone marrow to peripheral blood [Tables 1 and 2]. In the first experiment, after 2 days of treatment with the polypeptide of the present invention (CP), the frequency of HPP-CFC, LPP-CFC and immature cells in peripheral blood increased significantly over the controls. No changes were observed in the spleen and a significant decrement of HPP-CFC was observed in the bone marrow [Table 1]. In the second experiment, after 4 days of treatment with the polypeptide of the present invention (CP), the same significant increment of HPP-CFC, LPP-CFC and immature cells frequency was observed in peripheral blood. A significant increment of immature cells frequency was observed in the spleen and a significant decrement of HPP-CFC and LPP-CFC was observed in the bone marrow (Table 2). In particular it is important to note the presence of immature hematopoietic cells in the peripheral blood after the injection of the polypeptide of the present invention (CP). The effect observed in the animals treated with the polypeptide of the present invention (CP) was not due to toxicity as the FACScan profile of the leukocyte composition of both the control and the mice treated with the polypeptide of the present invention (CP) is identical (Table 3).

Example 6
CP as a Myeloprotectant against Cytosine Arabinoside

Figure 4B:
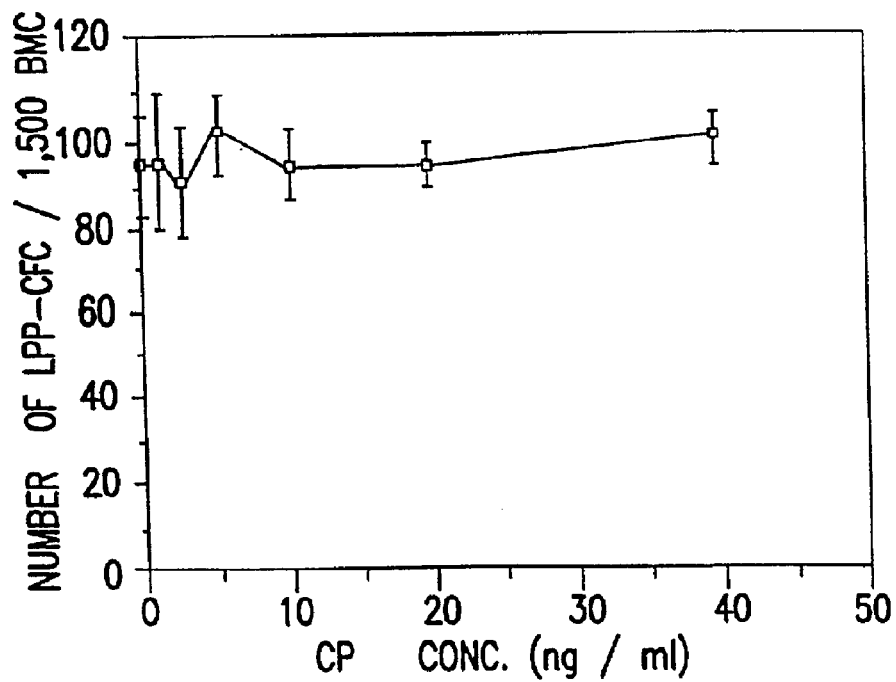
Figure 6:
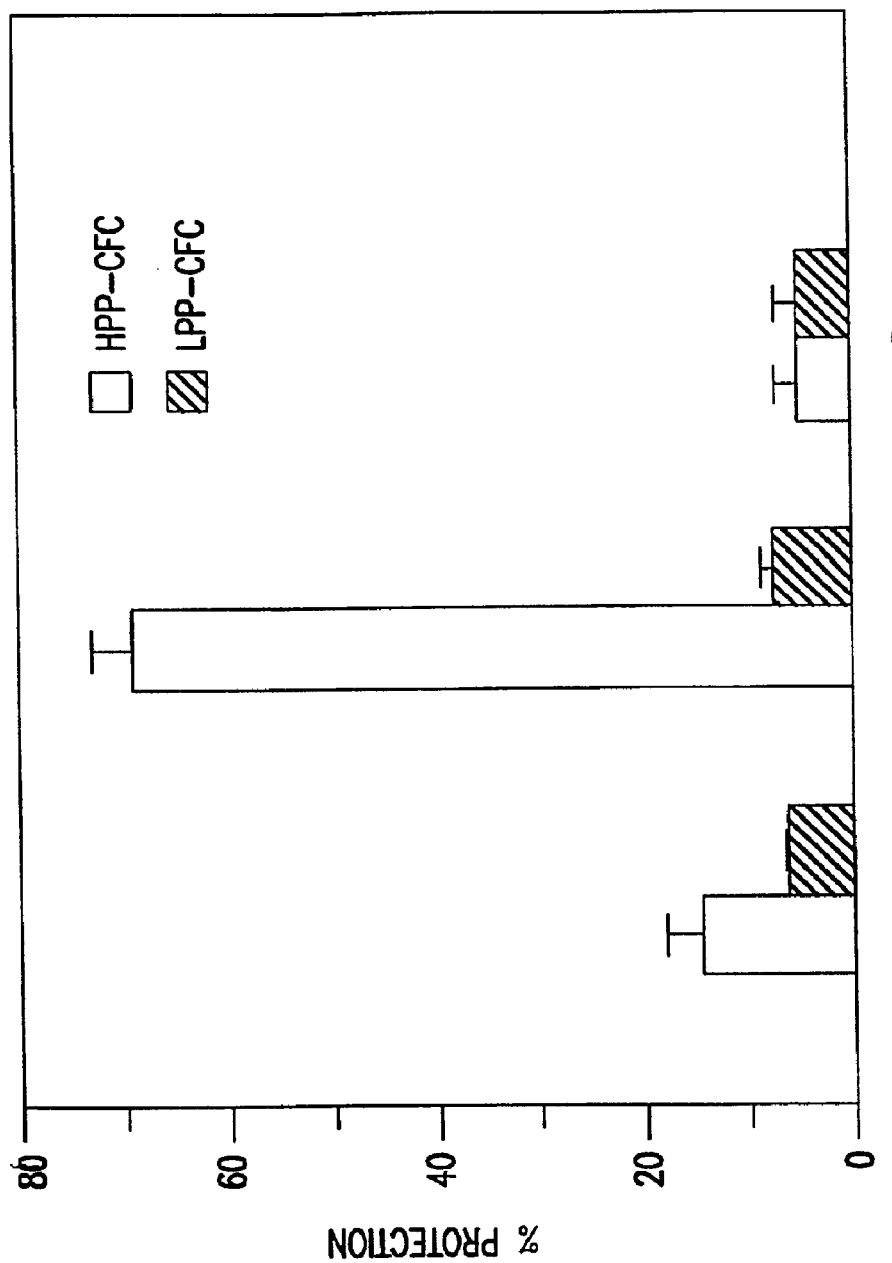
FIG. 6 illustrates that the polypeptide of the present invention (CP) protects HPP-CFC but not LPP-CFC from the cytotoxic effect of cytosine arabinoside (Ara-C) in vitro.

In this experiment, Lin-cells were plated ($1 \times 10^5$ cell/ml) in a growth medium that was supplemented with 5 ng/ml mouse IL-3, 50 ng/ml mouse SCF (column 1); IL-3, SCF and 100 ng/ml the polypeptide of the present invention (CP) (column 2); or IL-3, SCF and 100 ng/ml of the irrelevant protein HG200-3-B (column 3). After 48 hours of incubation, one set of the above cultures received 50 µg/ml Ara-C and the incubation was then continued for an additional 24 hours. Cells were then harvested, washed three times with HBSS to remove the drug and the cytokines, and assayed for the presence of HPP-CFC and LPP-CFC as described in the legend to FIGS. 4A–4B. The results are expressed as mean % of protection (±SD). The % of protection was calculated as follows: Percent protection is expressed as number of colonies found in cultures incubated in the presence of Ara-C divided by the number of colonies found in cultures incubated without Ara-C×100. Data from one out of 3 experiments are shown in FIG. 6. All the samples were tested in duplicates.

Example 7
CP as a Myeloprotectant against 5-Fluorouracil

Figure 5A:
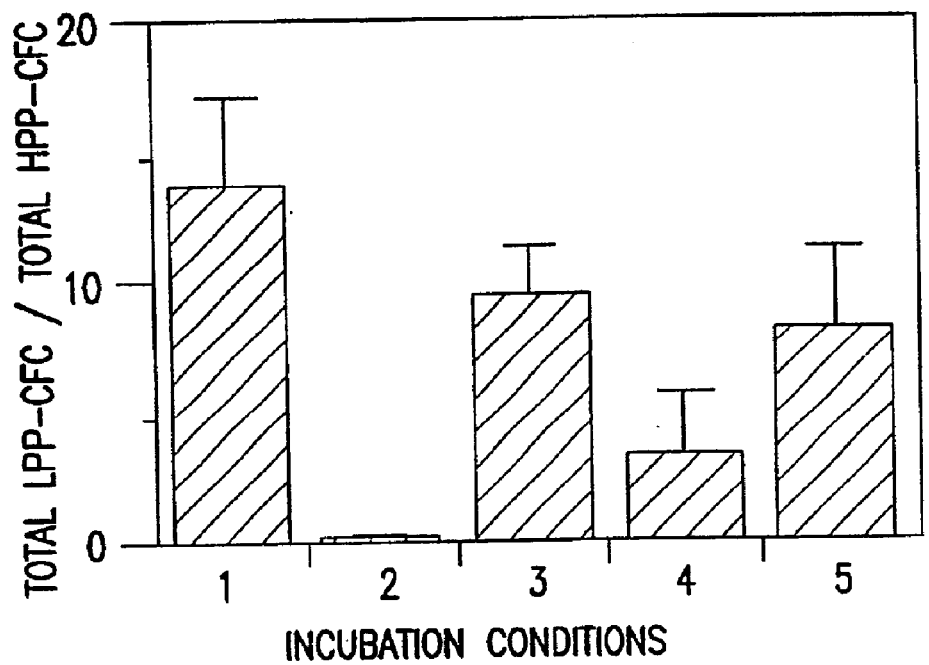
FIGS. 5A–5B show the effect of the polypeptide of the present invention (CP) on bone marrow cells which were enriched in the primitive Lin-cells by removing committed precursor cells (antibodies anti-CD11b, CD4, CD8, CD45R and Gr.-1). The panel A shows ratios ±SD of LPP-CFC/HPP-CFC in the bone marrow cells (column 1) or Lin-cells (column 2) plated in agar-medium with 5 ng/ml IL-3, 100 ng/ml SCF, 10 ng/ml IL-1a, 5 ng/ml M-CSF. Columns 3, 4 and 5 show the ratio of LPP-CFC/HPP-CFC found in the Lin- cells that were cultured with 5 ng/ml IL-3 and 100 ng/ml SCF (column 3), IL-3, SCF and 50 ng/ml of the polypeptide of the present invention (CP) (column 4) or IL-3, SCF and 50 ng/ml of an irrelevant protein (column 5). After 6 days, cultures were assayed for HPP-CFC and LPP-CFC. The panel B shows the cellularity after 6 days incubation.
Figure 5B:
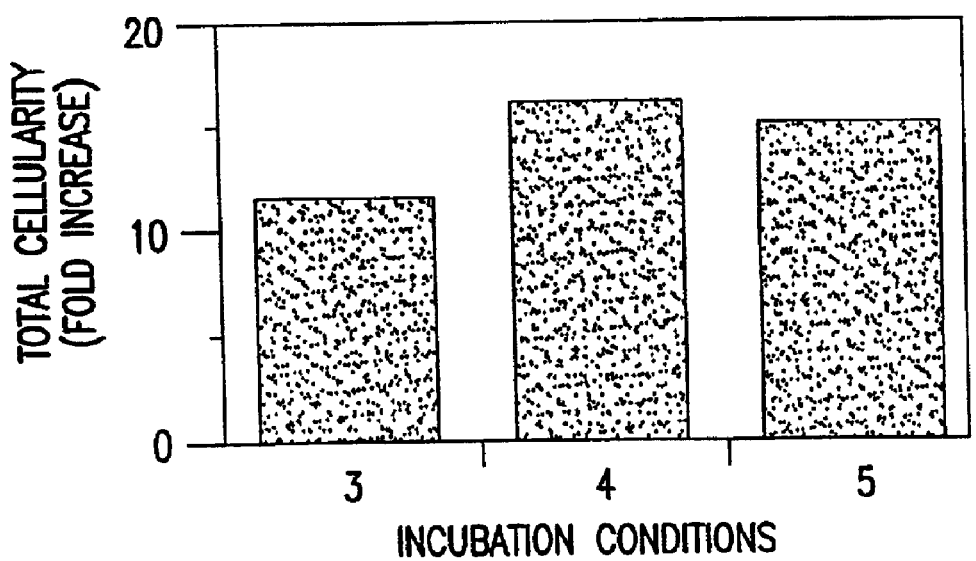
Figure 7:
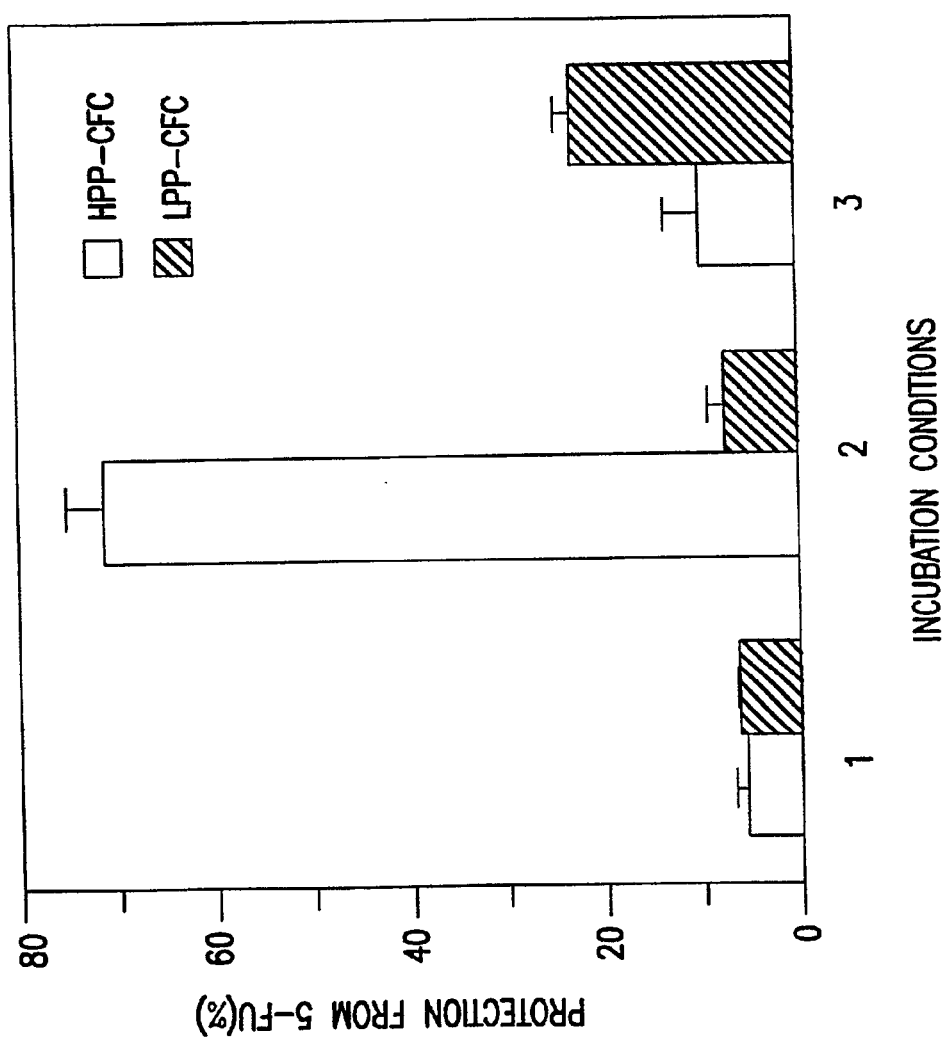
FIG. 7 illustrates that the polypeptide of the present invention (CP) protects HPP-CFC but not LPP-CFC from the cytotoxic effect of 5-Fluorouracil (5-FU) in vitro.

Mononuclear population of mouse bone marrow cells was depleted of lineage-committed cells by negative selection using a panel of monoclonal antibodies directed against cell surface antigens. The resulting population of cells (Lin.-cells) were resuspended ($1 \times 10^5$ cells/ml) in a growth medium containing IL-3 (5 ng/ml), SCF (50 ng/ml), GM-CSF (5 ng/ml), M-CSF (5 ng/ml) and IL-1α (10 ng/ml) and 1 ml of this cell suspension was dispensed into culture tubes. (1) A set of duplicate cultures received no chemokine; (2) duplicate cultures with the polypeptide of the present invention (CP) at 100 ng/ml; and (3) duplicate cultures with an irrelevant protein at 100 ng/ml. All cultures were incubated in a tissue culture incubator for 48 hours, at which point one culture from each set received 5-Fluorouracil at 100 µg/ml and incubation was continued for additional 24 hours. All cultures were then harvested, washed three times with HBSS, and then assayed for the presence of the HPP-CFC & LPP-CFC as described in the legend to FIGS. 5A–5B. Percent protection is expressed as number of colonies detected in cultures incubated in the presence of 5-FU divided by the number of colonies found in cultures incubated without 5-FU×100. Data are expressed as Mean±SD. Two experiments were performed and each assay was in duplicates. See FIG. 7.

Example 8
CP Effect on Cortical Neuronal Survival

Sprague-Dawley rats at gestation day 17 were sacrificed and the cortex was removed and the meninges were carefully peeled away from the cortical tissue pieces. Single cell suspensions were prepared and the cells were plated in medium containing 5% horse serum at a density of 20,000 cells/well. After 24 hours the serum containing medium was removed and serum-free medium was added to the cultures.

Figure 8:
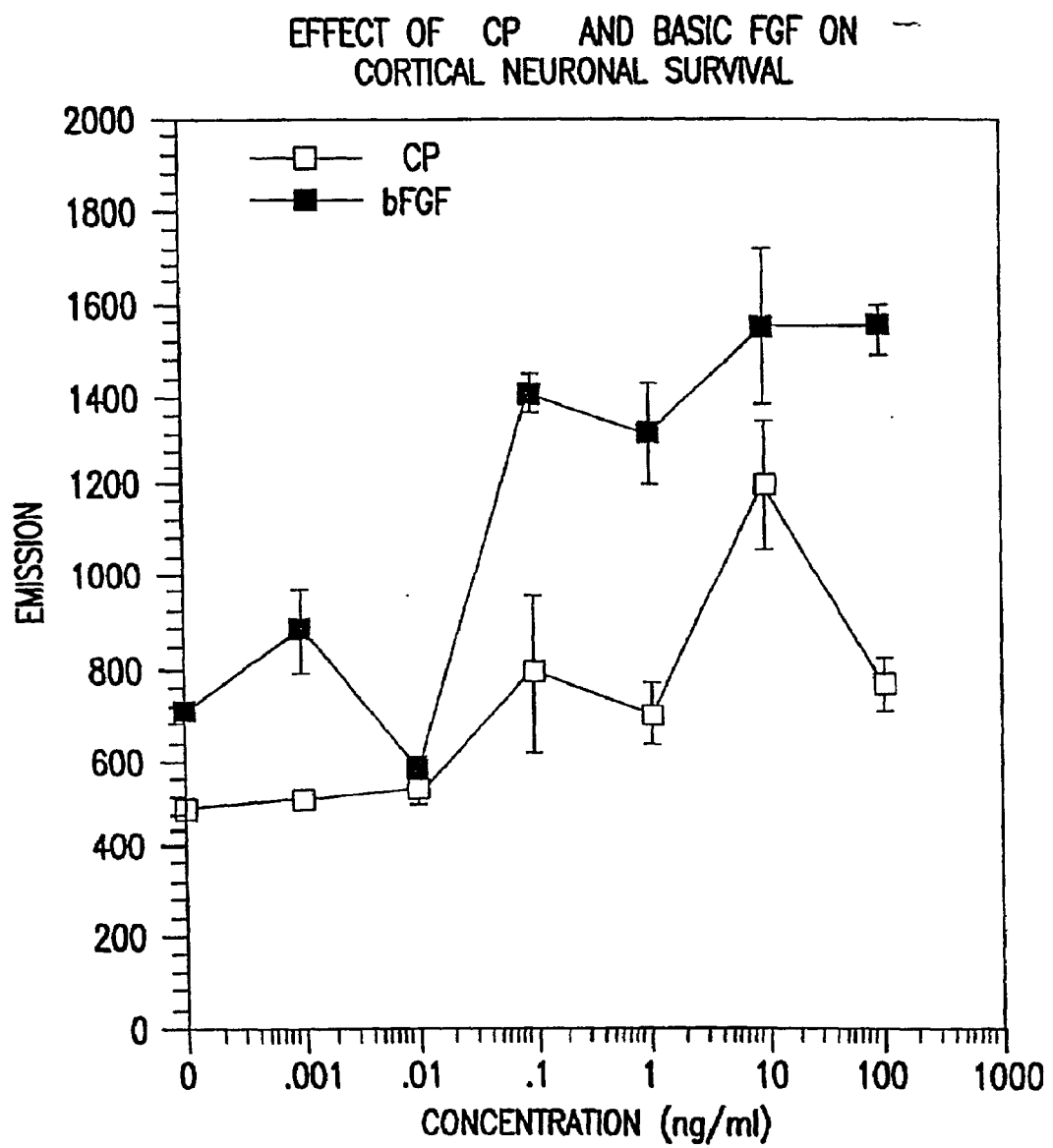
FIG. 8 illustrates the effect of the polypeptide of the present invention (CP) and Basic FGF on Cortical Neuronal Survival.

Included in the serum-free cultures was a concentration of the polypeptide of the present invention (CP) as shown in FIG. 8. The polypeptide of the present invention (CP) is encoded by the polynucleotide sequence as shown in SEQ ID NO:1 of the application. The medium was changed every other day and the polypeptide of the present invention (CP) was added again. The neurons were maintained in culture for 6 days prior to the viability assay.

Cell viability was assessed using the live/dead assay kit from Molecular Probes. This assay is a two-color fluorescence cell viability assay based on the simultaneous determination of live and dead cells. Live cells are distinguished by the presence of ubiquitous intracellular esterase activity, determined by enzymatic conversion of the nearly non-fluorescent cell permeant calcein AM to the intensely fluorescent calcein. The polycationic calcein is well retained by living cells and thus produces an intense uniform green fluorescence in living cells. Thus the emission reading (approximately 530 nm) is a measurement of the total cell number of the cultures. As shown in FIG. 8, the number of live cells increased as the concentration of the polypeptide of the present invention (CP) increased.

Numerous modifications and variations of the present invention are possible in light of the above teachings and, therefore, within the scope of the appended claims, the invention may be practiced otherwise than as particularly described.

What is claimed is:

1. An isolated antibody or fragment thereof that specifically binds to a protein selected from the group consisting of:
   (a) a protein consisting of amino acid residues −26 to 93 of SEQ ID NO:2;
   (b) a protein consisting of amino acid residues 1 to 93 of SEQ ID NO:2;
   (c) a protein consisting of a portion of SEQ ID NO:2, wherein said portion is at least 30 contiguous amino acid residues in length; and
   (d) a protein consisting of a portion of SEQ ID NO:2, wherein said portion is at least 50 contiguous amino acid residues in length.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 that specifically binds protein (d).

6. The antibody or fragment thereof of claim 2 that specifically binds protein (b).

7. The antibody or fragment thereof of claim 3 wherein said protein bound by said antibody or fragment thereof is glycosylated.

8. The antibody or fragment thereof of claim 3 which is a human antibody.

9. The antibody or fragment thereof of claim 3 which is a polyclonal antibody.

10. The antibody or fragment thereof of claim 3 which is selected from the group consisting of:

(a) a chimeric antibody;

(b) a humanized antibody;

(c) a single chain antibody; and (d) a Fab fragment.

11. The antibody or fragment thereof of claim 3 wherein said antibody or fragment thereof specifically binds to said protein in a Western blot.

12. The antibody or fragment thereof of claim 3 wherein said antibody or fragment thereof specifically binds to said protein in an ELISA.

13. An isolated cell that produces the antibody or fragment thereof of claim 3.

14. A hybridoma that produces the antibody or fragment thereof of claim 3.

15. A method of detecting human chemotactic protein in a biological sample comprising:

(a) contacting the biological sample with the antibody or fragment thereof of claim 3; and (b) detecting the human chemotactic protein in the biological sample.

16. The method of claim 15 wherein the antibody or fragment thereof is a polyclonal antibody.

17. An isolated antibody or fragment thereof obtained from an animal that has been immunized with a protein selected from the group consisting of:

(a) a protein comprising the amino acid sequence of residues −26 to 93 of SEQ ID NO:2;

(b) a protein comprising the amino acid sequence of residues 1 to 93 of SEQ ID NO:2;

(c) a protein comprising the amino acid sequence of at least 30 contiguous amino acid residues of SEQ ID NO:2; and (d) a protein comprising the amino acid sequence of at least 50 contiguous amino acid residues of SEQ ID NO:2;

wherein said antibody or fragment thereof specifically binds to said amino acid sequence.

18. The antibody or fragment thereof of claim 17 obtained from an animal immunized with protein (a).

19. The antibody or fragment thereof of claim 17 obtained from an animal immunized with protein (b).

20. The antibody or fragment thereof of claim 17 obtained from an animal immunized with protein (c).

21. The antibody or fragment thereof of claim 17 obtained from an animal immunized with protein (d).

22. The antibody or fragment thereof of claim 17 which is a monoclonal antibody.

23. The antibody or fragment thereof of claim 17 which is selected from the group consisting of:

(a) a chimeric antibody;

(b) a polyclonal antibody;

(c) a humanized antibody;

(d) a single chain antibody; and (e) a Fab fragment.

24. An isolated monoclonal antibody or fragment thereof that specifically binds to a protein selected from the group consisting of:

(a) a protein consisting of amino acid residues −26 to 93 of SEQ ID NO:2;

(b) a protein consisting of amino acid residues 1 to 93 of SEQ ID NO:2;

(c) a protein consisting of a portion of SEQ ID NO:2, wherein said portion is at least 30 contiguous amino acid residues in length; and (d) a protein consisting of a portion of SEQ ID NO:2, wherein said portion is at least 50 contiguous amino acid residues in length.

25. The antibody or fragment thereof of claim 24 that specifically binds protein (a).

26. The antibody or fragment thereof of claim 24 that specifically binds protein (b).

27. The antibody or fragment thereof of claim 24 that specifically binds protein (c).

28. The antibody or fragment thereof of claim 24 that specifically binds protein (d).

29. The antibody or fragment thereof of claim 25 that specifically binds protein (b).

30. The antibody or fragment thereof of claim 26 wherein said protein bound by said antibody or fragment thereof is glycosylated.

31. The antibody or fragment thereof of claim 26 which is a human antibody.

32. The antibody or fragment thereof of claim 26 which is selected from the group consisting of:

(a) a chimeric antibody;

(b) a humanized antibody;

(c) a single chain antibody; and (d) a Fab fragment.

33. The antibody or fragment thereof of claim 26 wherein said antibody or fragment thereof specifically binds to said protein in a Western blot.

34. The antibody or fragment thereof of claim 26 wherein said antibody or fragment thereof specifically binds to said protein in an ELISA.

35. An isolated cell that produces the antibody or fragment thereof of claim 26.

36. A hybridoma that produces the antibody or fragment thereof of claim 26.

37. A method of detecting human chemotactic protein in a biological sample comprising:

(a) contacting the biological sample with the antibody or fragment thereof of claim 26; and (b) detecting the human chemotactic protein in the biological sample.

38. An isolated antibody or fragment thereof that specifically binds to a protein selected from the group consisting of:

(a) a protein consisting of the full-length polypeptide encoded by the cDNA contained in ATCC Deposit Number 75703;

(b) a protein consisting of the mature form of the polypeptide encoded by the eDNA contained in ATCC Deposit Number 75703;

(c) a protein consisting of a portion of the polypeptide encoded by the cDNA contained in ATCC Deposit Number 75703, wherein said portion is at least 30 contiguous amino acid residues in length; and (d) a protein consisting of a portion of the polypeptide encoded by the cDNA contained in ATCC Deposit Number 75703, wherein said portion is at least 50 contiguous amino acid residues in length.

39. The antibody or fragment thereof of claim 38 that specifically binds protein (a).

40. The antibody or fragment thereof of claim 38 that specifically binds protein (b).

41. The antibody or fragment thereof of claim 38 that specifically binds protein (c).

42. The antibody or fragment thereof of claim 38 that specifically binds protein (d).

43. The antibody or fragment thereof of claim 39 that specifically binds protein (b).

44. The antibody or fragment thereof of claim 40 wherein said protein bound by said antibody or fragment thereof is glycosylated.

45. The antibody or fragment thereof of claim 40 which is a human antibody.

46. The antibody or fragment thereof of claim 40 which is a polyclonal antibody.

47. The antibody or fragment thereof of claim 40 which is selected from the group consisting of:
 (a) a chimeric antibody;
 (b) a humanized antibody;
 (c) a single chain antibody; and
 (d) a Fab fragment.

48. The antibody or fragment thereof of claim 40 wherein said antibody or fragment thereof specifically binds to said protein in a Western blot.

49. The antibody or fragment thereof of claim 40 wherein said antibody or fragment thereof specifically binds to said protein in an ELISA.

50. An isolated cell that produces the antibody or fragment thereof of claim 40.

51. A hybridoma that produces the antibody or fragment thereof of claim 40.

52. A method of detecting human chemotactic protein in a biological sample comprising:
 (a) contacting the biological sample with the antibody or fragment thereof of claim 40; and
 (b) detecting the human chemotactic protein in the biological sample.

53. The method of claim 52 wherein the antibody or fragment thereof is a polyclonal antibody.

54. An isolated antibody or fragment thereof obtained from an animal that has been immunized with a protein selected from the group consisting of:
 (a) a protein comprising the amino acid sequence of the full-length polypeptide encoded by the cDNA contained in ATCC Deposit Number 75703;
 (b) a protein comprising the amino acid sequence of the mature form of the polypeptide encoded by the cDNA contained in ATCC Deposit Number 75703;
 (c) a protein comprising the amino acid sequence of at least 30 contiguous amino acid residues of the polypeptide encoded by the cDNA contained in ATCC Deposit Number 75703; and
 (d) a protein comprising the amino acid sequence of at least 50 contiguous amino acid residues the polypeptide encoded by the cDNA contained in ATCC Deposit Number 75703;
 wherein said antibody or fragment thereof specifically binds to said amino acid sequence.

55. The antibody or fragment thereof of claim 54 obtained from an animal immunized with protein (a).

56. The antibody or fragment thereof of claim 54 obtained from an animal immunized with protein (b).

57. The antibody or fragment thereof of claim 54 obtained from an animal immunized with protein (c).

58. The antibody or fragment thereof of claim 54 obtained from an animal immunized with protein (d).

59. The antibody or fragment thereof of claim 54 which is a monoclonal antibody.

60. The antibody or fragment thereof of claim 54 which is selected from the group consisting of:
 (a) a chimeric antibody;
 (b) a polyclonal antibody;
 (c) a humanized antibody;
 (d) a single chain antibody; and
 (e) a Fab fragment.

61. An isolated monoclonal antibody or fragment thereof that specifically binds to a protein selected from the group consisting of:
 (a) a protein consisting of the full-length polypeptide encoded by the cDNA contained in ATCC Deposit Number 75703;
 (b) a protein consisting of the mature form of the polypeptide encoded by the cDNA contained in ATCC Deposit Number 75703;
 (c) a protein consisting of a portion of the polypeptide encoded by the cDNA contained in ATCC Deposit Number 75703, wherein said portion is at least 30 contiguous amino acid residues in length; and
 (d) a protein consisting of a portion of the polypeptide encoded by the cDNA contained in ATCC Deposit Number 75703, wherein said portion is at least 50 contiguous amino acid residues in length.

62. The antibody or fragment thereof of claim 61 that specifically binds protein (a).

63. The antibody or fragment thereof of claim 61 that specifically binds protein (b).

64. The antibody or fragment thereof of claim 61 that specifically binds protein (c).

65. The antibody or fragment thereof of claim 61 that specifically binds protein (d).

66. The antibody or fragment thereof of claim 62 that specifically binds protein (b).

67. The antibody or fragment thereof of claim 63 wherein said protein bound by said antibody or fragment thereof is glycosylated.

68. The antibody or fragment thereof of claim 63 which is a human antibody.

69. The antibody or fragment thereof of claim 63 which is selected from the group consisting of:
 (a) a chimeric antibody;
 (b) a humanized antibody;
 (c) a single chain antibody; and
 (d) a Fab fragment.

70. The antibody or fragment thereof of claim 63 wherein said antibody or fragment thereof specifically binds to said protein in a Western blot.

71. The antibody or fragment thereof of claim 63 wherein said antibody or fragment thereof specifically binds to said protein in an ELISA.

72. An isolated cell that produces the antibody or fragment thereof of claim 63.

73. A hybridoma that produces the antibody or fragment thereof of claim 63.

74. A method of detecting human chemotactic protein in a biological sample comprising:
 (a) contacting the biological sample with the antibody or fragment thereof of claim 63; and
 (b) detecting the human chemotactic protein in the biological sample.

75. An isolated antibody or fragment thereof that specifically binds human chemotactic protein purified from a cell culture wherein said human chemotactic protein is encoded by a polynucleotide encoding amino acids −26 to 93 of SEQ ID NO:2.

76. The antibody or fragment thereof of claim 75 which is a monoclonal antibody.

77. The antibody or fragment thereof of claim 75 which is a human antibody.

78. The antibody or fragment thereof of claim 75 which is selected from the group consisting of:

(a) a chimeric antibody;

(b) a polyclonal antibody;

(c) a humanized antibody;

(d) a single chain antibody; and (e) a Fab fragment.

79. The antibody or fragment thereof of claim 75 wherein said antibody or fragment thereof specifically binds to said protein in a Western blot.

80. The antibody or fragment thereof of claim 75 wherein said antibody or fragment thereof specifically binds to said protein in an ELISA.

* * * * *